United States Patent [19]
Brent et al.

[11] Patent Number: 6,017,692
[45] Date of Patent: Jan. 25, 2000

[54] METHODS OF DETECTING A MALIGNANT CELL IN A BIOLOGICAL SAMPLE COMPRISING MEASURING MXI GENE EXPRESSION ALTERATIONS

[75] Inventors: Roger Brent, Cambridge; Antonis S. Zervos, Boston, both of Mass.

[73] Assignee: The General Hospital Corporation, Boston, Mass.

[21] Appl. No.: 08/554,385

[22] Filed: Nov. 8, 1995

Related U.S. Application Data

[63] Continuation-in-part of application No. 08/011,398, Jan. 29, 1993, Pat. No. 5,512,473.

[51] Int. Cl.$^7$ ............................................... G01N 33/53
[52] U.S. Cl. ........................... 435/4; 435/6; 435/7.1
[58] Field of Search ...................... 435/4, 6, 7.1

[56] References Cited

U.S. PATENT DOCUMENTS

| | | | |
|---|---|---|---|
| 5,302,519 | 4/1994 | Blackwood et al. | 435/69.1 |
| 5,512,473 | 4/1996 | Brent et al. | 435/240.2 |

FOREIGN PATENT DOCUMENTS

| | | |
|---|---|---|
| 87/06940 | 11/1987 | WIPO. |
| 91/11719 | 8/1991 | WIPO. |

OTHER PUBLICATIONS

Alvarez et al., The Journal of Biological Chemistry, 266:15277–15285 (1991).
Barrett et al., Molecular and Cellular Biology, 12:3130–3137 (1992).
Beckmann et al., Genes & Development, 5:1057–1066 (1991).
Berberich et al., Genes & Development, 6:166–176 (1992).
Blackwell et al., Science, 250:1149–1151 (1990).
Blackwood et al., Science, 251:1211–1217 (1991).
Blackwood et al., Genes & Development, 6:71–80 (1992).
Blackwood et al., Current Opinion in Genetics and Development, 2:227–235 (1992).
Crews et al., Cell Growth & Differentiation, 3:135–142 (1992).
Dang et al., Proc. Natl. Acad. Sci. USA, 89:599–602 (1992).
Golemis et al., Molecular and Cellular Biology, 12:3006–3014 (1992).
Halazonetis et al., Science, 255:464–466 (1992).
Kato et al., Genes & Development, 6:81–92 (1992).
Kato et al., Molecular and Cellular Biology, 10:5914–5920 (1990).
Kerkhoff et al., Proc. Natl. Acad. Sci. USA, 88:4323–4327 (1991).
Lech et al., Cell, 52:179–184 (1988).
Lüscher et al., Molecular and Cellular Biology, 8:2504–2512 (1988).
Papoulas et al., The Journal of Biological Chemistry, 267:10470–10480 (1992).
Prendergast et al., Cell, 65:395–407 (1991).
Prendergast et al., Science, 251:186–189 (1991).
Vinson et al., The New Biologist, 4:396–403 (1992).
Zervos et al., Cell, 72:223–232, 1993.
Adams et al., Nature, 355:632–634 (1992).
Benezra et al., Cell, 61:49–59 (1990).
Berger et al., Cell, 70:251–265 (1992).
Brent et al., Nature, 312:612–615 (1984).
Brewster et al., Science, 259:1760–1763 (1993).
Cole, Ann. Rev. Genet. 20:361–384 (1986).
Dang et al., Mol. Cell. Biol., 8:4048–4054 (1988).
Derijard et al., Cell, 76:1025–1037 (1994).
Evan et al., Cell, 69:119–128 (1992).
Freytag et al., Mol. Cell. Biol., 8:1614–1624 (1988).
Gill et al., Nature, 334:721–724 (1988).
Gille et al., Nature, 358:414–417 (1992).
Gyuris et al., Cell, 75:791–803 (1993).
Halazonetis et al., Proc. Natl. Acad. Sci. USA, 88:6162–6166 (1991).
Han et al., Science, 265:808–811 (1994).
Hanks et al., Methods Enzymol., 200:38–62 (1991).
Hann et al., Mol. Cell. Biol., 4:2486–2497 (1984).
Harris et al., J. Leukocyte Biol., 37:407–422 (1985).
Hermeking et al., Science, 265:2091–2096 (1994).
Hu et al., Genes & Development, 4:1741–1752 (1990).
Kyriakis et al., Nature, 369:156–160 (1994).
Lee et al., Nature, 372:739–746 (1994).
Lüscher et al., Genes & Development, 4:2025–2036 (1990).
Ma et al., Cell, 51:113–119 (1987).
Marais et al., Cell, 73:381–393 (1993).
Miner et al., Mol Cell. Biol., 11:2842–2851 (1991).
O'Shea et al., Science, 243:538–542 (1989).
Rosenberg et al., N. Engl. J. Med., 323:570 (1990).
Shi et al., Science, 257:212–214 (1992).
Watanabe et al., Biochem. Biophys. Res. Comm., 126:999–1005 (1985).
Yan et al., Nature, 372:798–800 (1994).
Zhang et al., Nature, 367:704–711 (1994).

*Primary Examiner*—Prema Mertz
*Attorney, Agent, or Firm*—Clark & Elbing LLP

[57] ABSTRACT

Disclosed are substatially pure Reparations of Max-Interacting (Mxi) polypeptides, DNA encoding such polypeptides, antibodies recognizing such polypeptides, and diagnostic and therapeutic methods utilizing such polypeptides.

8 Claims, 11 Drawing Sheets

```
AGATTATGATGCGCCTGAGGCCCCTCTCCTACCCAGATACCGATGTTATACTGATGTGTTTTCCTTTTTTTTTTTAAGTAATAATTAAGGTAGTTAAATTATTTAAAGTATACA        120
AAGTCCAAACAGCCAGGGGGTAAGGTCTCCAAGAGCCCTTCCCCAGGGAGTGCCGAGAGCCCCCATGGAGCGGGTGAAGATGATCAACGTGCCAGCG                          240
                                                                                      M  P  S  P  R  R  L          15
TCTGCTGGAGGCTGCCGAGTTTTGGAGCGCCGGAGAGAGTGTTCAGCATGCCCAGCCCCCGACTGCAGCATTCAAAGCCCCCACGGAGGTTG                                360
 S  R  A  Q  K  H  S  S  G  T  S  N  T  S  T  A  N  R  S  T  H  N  E  L  E  K  N  R  R  A  H  L  R  L  C  L  E  R  L  K   55
AGCCGGGCACAGAAAACACAGCCAGCGACGGAGCGAGAGTGTGAACATCGTACACACAGATCTACACACAGACTCTGCCAACAGATCTACACAGACTCGCGCTTTGTTAGAACGCTTAAAA        480
 V  L  I  P  L  G  P  D  C  T  R  H  T  T  L  G  L  L  N  K  A  K  A  H  I  K  K  L  E  E  A  E  R  K  S  Q  H  Q  L  E   95
GTTCTGATTCCACTAGGACCCGACTGCACCAGAGACACAACACTGGTTGCTCAACAAAGCCAAAGCACACATCAAGAAACTGAAGAAAAAGCCAGACCAGCTCGAG                  600
 N  L  E  R  E  Q  R  F  L  K  W  R  L  E  Q  L  Q  G  P  Q  E  M  E  R  I  R  M  D  S  I  G  S  T  I  S  S  D  R  S  D  135
AATTTGGAACGCGAGCAGAGATTTTTAAAGTGGCGACTGGAACAGCTGCAGGGTCCTCAGGAGATGGAACGAATACGATTGGACACAGCATTGGATCAACTATTTCTTCAGATCGTTCTGAT  720
 S  R  E  E  I  E  V  D  V  E  S  T  E  F  S  H  G  E  V  D  N  I  S  T  S  I  S  D  I  D  D  H  S  S  L  P  S  I          175
TCAGAGCGAGAGGAGATTGAAGTGGATGTTGAAAGCACAGAGTTCTCCCATGGAGAAGTGGACAATAAGTACCACCAGCATCAGTGACCATTGATGACCAGCAGCTTGCCAGTATT       840
 G  S  D  E  G  Y  S  S  A  S  V  K  L  S  F  T  S  Y  R  T  Q  H  D  I  T  V  Q  G  K  I  F  T  G  P  I  Q  Y  K  Q  S  215
GGGAGTGACGAGGGTTACTCCAGTGCCAGTGTTCAAACTTTCATTCATTCTATTCTTCATTCATTTCATTCATTCACTTCACTGCTCACTGSSCCAATTCAATACAACAATCT           960
 L  K  L  G  S  *                                                                                                          220
CTTAAATTGGGGTTCATGATGCAGTCAGTCTCCCTCTCTTAAACAACAAACAAAACAAAAACTATACTTGAACACAAAACAAAAGGGTCAGAGGACCTGTATTAAGCAAATACTTAGCAAAAGTGGGC  1080
AGAGCCTCCAAGGAGAACAAATATTCAGAATATTTCATATTGGAAAAATCACAATTTTTAAGCAGCAAATTGTGTGAAATTTCTGATTGAGTTGAATGAGAAGAGACATTG          1200
GAGATGCCATCCTCCTTCTCTTTTCGTTTTGCTCATACTACATTGAGTAGACACACATTTAAGGATGGGGTTATGAACCCTTCCTGAGCTTTAAGCCTGGGATGATCAAAAGCAAAAATAAAAACTATT  1320
CGAATGAAAAGACAAGAAAGCTCATTTGAACTCTGCAAAAGGAGGATCATCATGAGCTAGCAGTTTATCATCATCAACTTCTGTTCTTTTCATGTCATGCTAAGCAAGCTAACCT         1440
TTTTTGAAAAAAGCTTGTTAGCACTAGGCACCAGCCCTCCTTTGCTCCTTTGGGTGCCTCTTTGCTCGTGGGGTCAGAATTAGCACGCAGATTAGCACGCGAAGTCGCACCGCAAGGTCTGCAGGGAAAAACACATGG      1560
TATCCCTGCATTGTTAGCCAAAAAGGCAAAAGAAAAAGCTCCATGCCATGCATTTTAAAGCTTCATTCTAGATCATCTTTTTAAGCTTATCCATAAAATGAATGAAAAAAATGAAGAAAAAAATCATCTATTTTGATGCA  1680
TAACTGTTTTATATGTTGAAAAGGCAAAAGGTCAAAAGGTCCAAAAGCCCAAAAATGATAAAACACCTCACACCTCACTCTTAGGTAGTGCACAAAAATGAATGAGGTCTGGCTAGGTAGAAAAAAGGGTCAATGCTATTTTTGTTTTTTAGAATCATCATTACCTTTA   1920
GCATTTGATAATGATAAAACTGAAAATGCACAAATCCAAGTGTCTGGCTAGGTAGAAAAAAGGGTCAATGCTATTTTTGTTTTTTAGAATCATCATTACCTTTA           2040
CCAGCTTTTAACCATCTGATATCTATAGTAGACACACTATCATAGTTAACATAGTTAACATAGAATTGTCTCCATTTTAATGTAAAGATTTGCTTCCACTGCACCAGCAGTCTC            2160
TCTTCCTCACAGTCCCCACTGTCCGCAGGTGTCATTGTTACTCTTACGAATGTTATTTTCTTAAGTAATGTAATATTTTCAGTGAATTCTAGCCTGCATGTGTTCCCTTGTC              2280
TTTCAAACTCCAAGGTTCCCCTGGTGGCCCCTCCCCTGGGTGTTTGGACTTTGTATACTTTAAATAATTAACTACCCTTAATTACT                                        2400
TAAAAAAAAAAAAA  2417  (SEQ ID NO: 1 AND 2)
```

Fig. 2

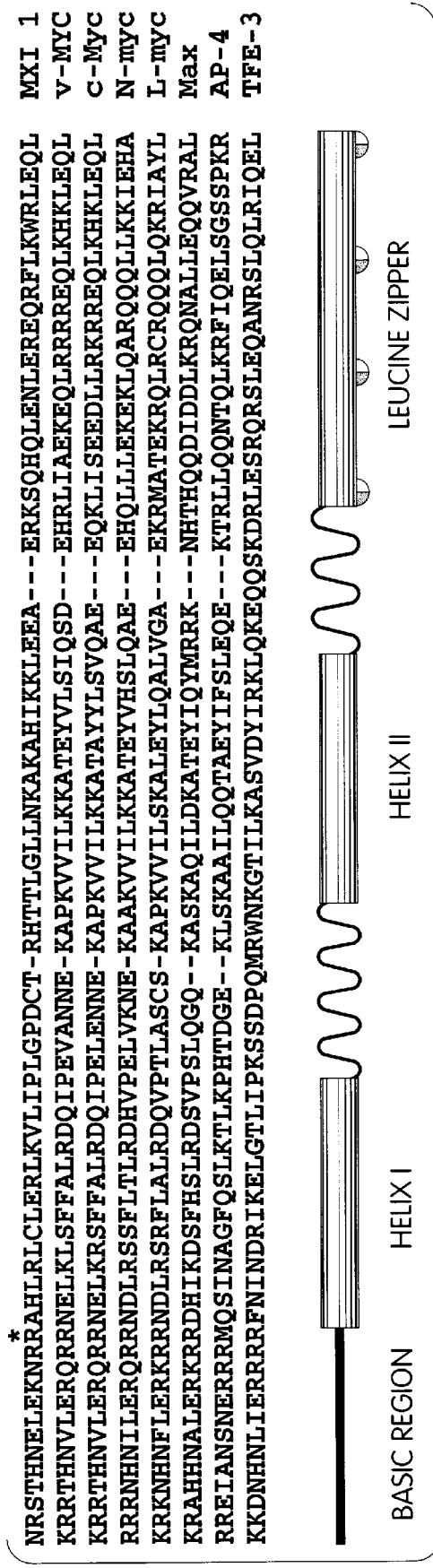
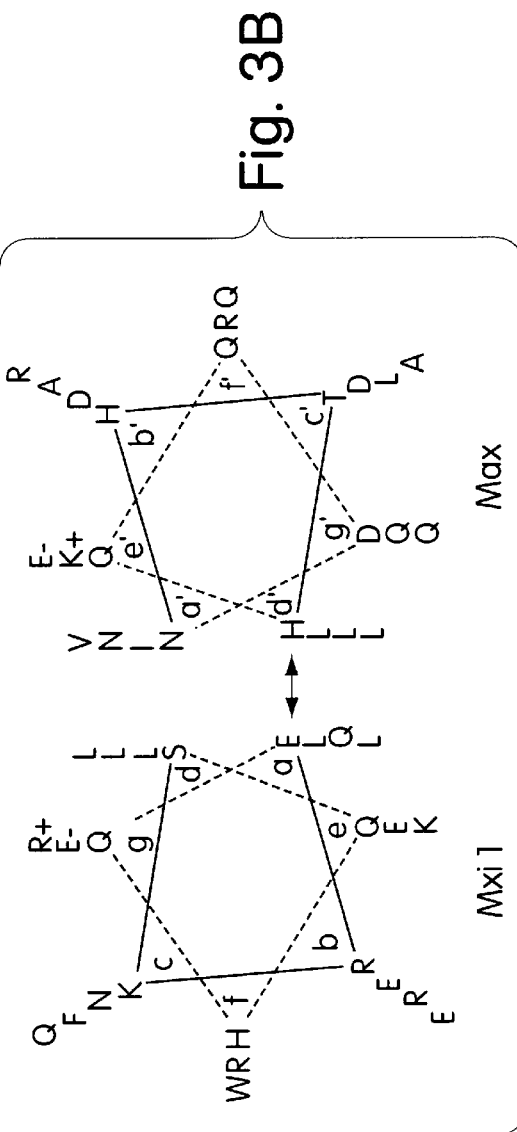
Fig. 3A
Fig. 3B

```
GAATTCGGCACGAGGCGCCTTCTTGCCCGGCGGCTGCTGGAAAATGTCTCAGGAGAGGCC
                                              M  S  Q  E  R  P
CACGTTCTACCGGCAGGAGCTGAACAAGACAATCTGGGAGGTGCCCGAGCGTTACCAGAA
 T  F  Y  R  Q  E  L  N  K  T  I  W  E  V  P  E  R  Y  Q  N

CCTGTCTCCAGTGGGCTCTGGCGCCTATGGCTCTGTGTGTGCTGCTTTTGACACAAAAAC
 L  S  P  V  G  S  G  A  Y  G  S  V  C  A  A  F  D  T  K  T

GGGGTTACGTGTGGCAGTGAAGAAGCTCTCCAGACCATTTCAGTCCATCATTCATGCGAA
 G  L  R  V  A  V  K  K  L  S  R  P  F  Q  S  I  I  H  A  K

AAGAACCTACAGAGAACTGCGGTTACTTAAACATATGAAACATGAAAATGTGATTGGTCT
 R  T  Y  R  E  L  R  L  L  K  H  M  K  H  E  N  V  I  G  L

GTTGGACGTTTTTACACCTGCAAGGTCTCTGGAGGAATTCAATGATGTGTATCTGGTGAC
 L  D  V  F  T  P  A  R  S  L  E  E  F  N  D  V  Y  L  V  T

CCATCTCATGGGGGCAGATCTGAACAACATTGTGAAATGTCAGAAGCTTACAGATGACCA
 H  L  M  G  A  D  L  N  N  I  V  K  C  Q  K  L  T  D  D  H

TGTTCAGTTCCTTATCTACCAAATTCTCCGAGGTCTAAAGTATATACATTCAGCTGACAT
 V  Q  F  L  I  Y  Q  I  L  R  G  L  K  Y  I  H  S  A  D  I

AATTCACAGGGACCTAAAACCTAGTAATCTAGCTGTGAATGAAGACTGTGAGCTGAAGAT
 I  H  R  D  L  K  P  S  N  L  A  V  N  E  D  C  E  L  K  I

TCTGGATTTTGGACTGGCTCGGCACACAGATGATGAAATGACAGGCTACGTGGCCACTAG
 L  D  F  G  L  A  R  H  T  D  D  E  M  T  G  Y  V  A  T  R

GTGGTACAGGGCTCCTGAGATCATGCTGAACTGGATGCATTACAACCAGACAGTTGATAT
 W  Y  R  A  P  E  I  M  L  N  W  M  H  Y  N  Q  T  V  D  I

TTGGTCAGTGGGATGCATAATGGCCGAGCTGTTGACTGGAAGAACATTGTTTCCTGGTAC
 W  S  V  G  C  I  M  A  E  L  L  T  G  R  T  L  F  P  G  T

AGACCATATTGATCAGTTGAAGCTCATTTTAAGACTCGTTGGAACCCCAGGGGCTGAGCT
 D  H  I  D  Q  L  K  L  I  L  R  L  V  G  T  P  G  A  E  L

TTTGAAGAAAATCTCCTCAGAGTCTGCAAGAAACTATATTCAGTCTTTGACTCAGATGCC
 L  K  K  I  S  S  E  S  A  R  N  Y  I  Q  S  L  T  Q  M  P

GAAGATGAACTTTGCGAATGTATTTATTGGTGCCAATCCCCTGGGTAAGTTGACCATATA
 K  M  N  F  A  N  V  F  I  G  A  N  P  L  G  K  L  T  I  Y

TCCTCACCTCATGGATATTGAATTGGTTATGATATAAATTGGGGATTTGAAGAAGAGTTT
 P  H  L  M  D  I  E  L  V  M  I  *

CTCCTTTTGACCAAATAAAGTACCATTAGTTGAAAAAAAAAAAAAAAAAAAAAAAAAAAA
AAA
```

Fig. 7

```
                        I                                II                            III
Mxi2    MSQERPTFYRQELNKTIWEVPERYQNLSPVGSGAYGSVCAAFDTKTGLRVAVKKLSRPFQSIIHAKRTYRELRLLK
p38     ----------------------------------------------------------------------------
Hog1    MTTNEE-I--TQIFGTVF-ITN--ND-N----M-F-L--S-T---L-SQP-I---IMK--STAVL-------K---

IV                            V                         VIA               VIB
        HMKHENVIGLLDVFTPARSLEEFNDVYLVTHLMGADLNNIVKCQKLTDDHVQFLIYQILRGLKYIHSADIIHRDLK
        ----------------------------------------------------------------------------
        -LR----L--C-Q--I-......-SPLE--I-F--E-Q-T--HRLLQTRP--EKQF--YFL--------V--GV----

VII                              VIII                       IX
        PSNLAVNEDCELKILDFGLARHTDDEMTGYVATRWYRAPEIMLNWMHYNQTVDIWSVGCIMAELLTGRTLFPGTDHI
        ----------------------------------------------------------------------------
        ---ILI--N-D---C-----IQDPQ-----S--Y------T-QK-DVE----A--F--MIE-KP----K--V

X                                                    XI
        DQLKLILRLVGTPGAELLKKISSESARNYIQSLTQMPKMNFANVFIGANPLGKLTIYPHLMDIELVMI*..........
        ...........................................AVDLLEKMLVLDSDKRITAAQALAHAY
        H-FSI-TD-L-S-PKDVINTIC--NTLKFVTS-PHRDPIP-SER-KTVE-D-------F-PK-----D----P-

FAQYHDPDDEPVADP.YDQSFESRDLLIDEWKSLTYDEVISFVPPPLDQEEMES*...............
        ......................................................................
        S--P-----T-----AKF-WH-NDA--PV-T-RVMM-S--ILD-HKIGGSDGQIDISATFDDQVAAATAAAAQAQAQAQAQ

............................
        ............................
        VQLNMAAHSHNGAGTTGNDHSDIAGGNKGQRSCSCK*
```

Fig. 8

METHODS OF DETECTING A MALIGNANT CELL IN A BIOLOGICAL SAMPLE COMPRISING MEASURING MXI GENE EXPRESSION ALTERATIONS

This application is a continuation-in-part of U.S. Ser. No. 08/011,398 filed Jan. 29, 1993, now U.S. Pat. No. 5,512,473.

BACKGROUND OF THE INVENTION

This invention relates to cancer diagnostics and therapeutics.

Members of the Myc protein family are involved in the formation of many cancers; in model systems, their heightened expression can induce oncogenic transformation (for reviews, see Cole, Genet 20:361–384, 1986; Lüscher and Eisenman, Genes and Development 4:2025–2035, 1990) and apoptosis (Evan et al., 1992; Cell 69:119–128, 1992; Shi et al., Science 257:212–214, 1992), and it can block differentiation (Freytag, Mol. Cell. Biol. 8:1614–1624, 1988; Miner and Wold, Mol. Cell Biol. 11:2842–2851, 1991). Of the Myc proteins, the best studied are probably the c-myc and v-myc products (cMyc and vMyc). These proteins are localized to the nucleus (Dang and Lee, Mol. Cell. Biol. 8:4048–4054, 1988) and activate transcription in transfection experiments when brought to DNA by heterologous DNA binding domains (Lech and Brent, Cell 52:179–184, 1988; Kato et al., Mol. Cell. Biol. 10:5914–5920, 1990; Golemis and Brent, Mol. Cell. Biol. 72:3006–3014, 1992). These proteins contain an activation domain in their amino terminus whose integrity is correlated with Myc's ability to cause oncogenic transformation (Kato et al., 10:5914–5920, 1990; Barrett et al., Mol. Cell. Biol. 12, 3130–3137, 1992. The proteins also contain a conserved structure, the basic region helix loop helix leucine zipper (hHLH-Zip) (reviewed in Vinson and Garcia, The New Biologist 4(4) :396–403, 1992), which directs dimerization and DNA recognition (Dang et al., Proc. Natl. Acad. Sci. USA. 89:599–602, 1992; Blackwell et al., Science 250:1149–1151, 1990; Halazonetis and Kandil, Science 255:464–466, 1992). These facts suggest that the biological function of cMyc and vMyc might depend on their ability to bind specific sequences and activate transcription.

This hypothesis has been greatly strengthened by the isolation of Max, a human protein that forms tight heterodimers with cMyc (Blackwood and Eisenman, Science 251:1211–1217, 1991), and the discovery of its murine homolog, Myn (Prendergast et al., Cell 65:395–407, 1991). Max was cloned using an in vitro method that depended on its ability to interact with the cMyc bHLH-Zip (Blackwood and Eisenman, Science 251:1211–1217, 1991). Max protein and mRNA are expressed in all tissues in which cMyc is expressed, and some, including the brain, in which it is not. Two different forms of the protein are encoded from differently spliced transcripts, a 151 amino acid protein (here called $Max_{1-151}$ or simply Max) and a larger form (here called $Max_{1-160}$) that contains an additional 9 amino acids at the amino terminus of the basic region. Max is localized to the cell nucleus, possibly due to a nuclear localization signal that is present at its carboxy terminus (Kato et al., Genes and Development 6:81–92, 1992). Max has a longer half life than cMyc (>24 h vs 30 min) (Blackwood et al., Genes and Development 6:71–80, 1992; Hann and Eisenman, Mol. Cell. Biol. 4:2486–2497, 1984; Luscher and Eisenman, Mol. Cell. Biol. 8:2504–2512, 1988).

Like Myc proteins, Max contains a bHLH-Zip motif. In Max, this region serves two functions; the helix loop helix and leucine zipper cause Max to form heterodimers with cMyc; and the basic region and residues near it make specific contacts with DNA. Max can form heterodimers with other members of the Myc family (Blackwood and Eisenman, Science 251:1211–1217, 1991) but does not interact with other known bHLH-Zip proteins (Blackwood and Eisenman, Science 251:1211–1217, 1991). Myc/Max heterodimers bind tightly to a consensus CACGTG sequence (Blackwood and Eisenman, Science 251:1211–1217, 1991; Prendergast et al., Cell 65:395–407, 1991). Myc/Myc homodimers bind the same sequence less tightly (Blackwell et al., Science 250:1149–1151, 1990; Prendergast and Ziff, Science 251:186–189, 1991; Kerkhoff et al., Proc. Natl. Acad. Sci. USA. 88:4323–4327, 1991; Halazonetis and Kandil, Science 255:464–466, 1992; Papoulas et al., The Journal of Biological Chemistry, 267 15:10470–10480, 1992) presumably because the native protein does not form homodimers readily, so that site recognition occurs only at high protein concentrations. Phosphorylation of Max by casein kinase abolishes DNA binding by Max/Max homodimers but not by cMyc/Max heterodimers, apparently by a direct effect on Max DNA recognition (Berberich and Cole, Genes and Development 6:166–176, 1992).

Because most cMyc in vivo is associated with Max, and because cMyc/Max heterodimers bind the CACGTG site more tightly than cMyc/cMyc homodimers (Blackwood and Eisenman, Science 251:1211–1217, 1991; Prendergast et al., Cell 65:395–407, 1991), it appears likely that one of the functions of Max is to facilitate the binding of cMyc to these sites. It is also possible that association with Max modulates cMyc's gene regulatory function; consistent with this idea, we have recently shown that Max is transcriptionally inert, but that association with Myc greatly potentiates the strength of the cMyc activation function.

These facts have led to a picture of Myc and Max dependent oncogenesis, in which cMyc complexes with Max and binds to sites upstream of genes whose transcription are regulated. In this view, changes in transcription dependent on this complex could be caused by changes in site recognition, by changes in the availability of cMyc or Max, and by modifications to cMyc and Max that alter their ability to oligomerize or that affect their transcription regulatory function. Each of these modulatory steps may be regulated by other cellular proteins, including oncoproteins, which may change the expression or phosphorylation state of the proteins (reviewed in Blackwood et al., Curr. Opin. Genet. Dev. 2:227–235, 1992.

SUMMARY OF THE INVENTION

In general, the invention features a substantially pure preparation of an Mxi polypeptide. Examples of Mxi polypeptides are shown in FIG. 2 (SEQ ID NO: 1) and in FIG. 7 (SEQ ID NO: 3). Preferably, such an Mxi polypeptide is derived from a mammal, for example, a human; and is Mxi1 or Mxi2 (for example, a sequence that is substantially identical to the sequence of FIG. 7; and is an ERK kinase).

In a related aspect, the invention features purified DNA (for example, cDNA) which includes a sequence encoding an Mxi polypeptide, and preferably a human Mxi polypeptide (for example, Mxi1 or Mxi2). One purified Mxi-encoding DNA according to the invention is shown in FIG. 2 (SEQ ID NO: 2); nucleotides 345–1020 encode the Mxi polypeptide. Another Mxi-encoding DNA according to the invention is shown in FIG. 7 (SEQ ID NO: 4).

In other related aspects, the invention features a vector and a cell which includes a purified Mxi-encoding DNA of the invention; a purified antibody which specifically binds an Mxi polypeptide of the invention; and a method of producing a recombinant Mxi polypeptide involving, providing a cell transformed with DNA encoding an Mxi polypeptide positioned for expression in the cell; culturing the transformed cell under conditions for expressing the DNA; and isolating the recombinant Mxi polypeptide. The invention further features recombinant Mxi polypeptide produced by such expression of a purified DNA of the invention.

In yet another aspect, the invention features a method of inhibiting cell (e.g., monocytic cell) proliferation in a mammal, involving administering to the mammal a nucleic acid encoding an Mxi polypeptide, the polypeptide being positioned for expression in the mammal. Preferably, the nucleic acid is part of a retroviral vector.

In yet another aspect, the invention features a method of detecting a malignant cell in a biological sample, involving measuring Mxi gene expression in the sample, a change in Mxi expression relative to a wild-type sample being indicative of the presence of a malignancy.

In a final aspect, the invention features a method for identifying a compound which inhibits cell proliferation. The method involves contacting a candidate compound with an Mxi polypeptide of the invention and measuring Mxi activity, a change in Mxi activity being indicative of a proliferation-inhibitory compound. In preferred embodiments, the Mxi polypeptide is expressed in a recombinant cell which includes a purified Mxi-encoding DNA of the invention, and the cell or a cell extract is contacted with the candidate compound; the activity is the Mxi polypeptide's ability to interact with a Max protein (for example, as measured using the interaction trap described herein); and the activity measured is protein kinase activity (for example, as described for Mxi2).

By "Mxi polypeptide" is meant a chain of amino acids capable of interacting with a Max protein in the interaction trap system described herein. Mxi polypeptides do not include Myc, Myn or Mad proteins. Preferably, an Mxi polypeptide according to the invention is related in sequence to the Mxi polypeptides of FIG. 2 or FIG. 7.

By "substantially pure" is meant a preparation which is at least 60% by weight (dry weight) the compound of interest, e.g., an Mxi polypeptide. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "substantially identical" is meant a polypeptide exhibiting at least 50%, preferably 70%, more preferably 90%, and most preferably 95% identity to a reference amino acid or is meant a nucleic acid sequence exhibiting at least 85%, preferably 90%, more preferably 95%, and most preferably 97% identity to a reference nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 30 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "purified DNA" is meant DNA that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) an Mxi polypeptide.

By "positioned for expression" is meant that the DNA molecule is positioned adjacent to a DNA sequence which directs transcription and translation of the sequence (i.e., facilitates the production of, e.g., an Mxi polypeptide).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody, e.g., Mxi-specific antibody. A purified Mxi antibody may be obtained, for example, by affinity chromatography using recombinantly-produced Mxi polypeptide and standard techniques.

By "specifically binds" is meant an antibody which recognizes and binds Mxi polypeptide but which does not substantially recognize and bind other molecules in a sample, e.g., a biological sample, which naturally includes Mxi polypeptide.

By a "malignant cell" is meant a cell which has been released from normal cell division control. Included in this definition are transformed and immortalized cells.

By "monocytic cell" is meant any cell of monocytic or premonocytic lineage.

Other features and advantages of the invention will be apparent from the following detailed description thereof, and from the claims.

DESCRIPTION OF THE DRAWINGS

FIG. 2 shows the nucleotide sequence and the deduced amino acid sequence of an Mxi1 cDNA (SEQ ID NOS: 1 and 2). The sequence of a 2417 nucleotide cDNA was determined by dideoxy sequencing of the complete sequence of two clones, the first one isolated in the yeast screen using an activation tagged HeLa expression library and encoding residues 10–220 corresponding to nucleotides 345–1020, and the second, a longer clone isolated from a HeLa library in lambda ZapII.

FIGS. 3A–3B illustrates Mxi1 bHLH-Zip. FIG. 3a shows a comparison of the bHLH-Zip region from Mxi1 residue 32 to residue 112 to bHLH-Zip regions of other proteins (SEQ ID NOS: 12–19). Amino acids present in Mxi1 and at least one other member of the set (cMyc, Max, avian vMyc, human nMyc and 1Myc, AP-4, and TFE-3) are shown in boldface. The C-terminal arginine within the basic region, which in cMyc specifies interaction with the CG core of the CACGTG consensus recognition sequence is shown with an asterisk (Halazonetis and Kandil, Science 255:464–466, 1992; Dang et al., Proc. Natl. Acad. Sci. USA. 89:599–602, 1992). Sequences of the Myc family bHLH-Zip were taken from Benezra et al. (Cell 61:49–59, 1990), Max from Blackwood and Eisenmann (Science 251:1211–1217, 1991), AP-4 from Hu et al. (Genes Dev. 4:1741–1752, 1990), and TFE-3 from Beckmann et al. (Genes Dev. 5:1057–1066, 1991). FIG. 3b shows the leucine zippers of Mxi1 and Max. These leucine zippers are each shown projected onto a helical wheel as in O'Shea et al. (Science 243:538–542, 1989). Boldface indicates residues of opposite charge at the g position of Mxi1 and the e' position of Max. The arrow indicates the glutamic acid at the amino terminus of the Mxi1 leucine zipper (Mxi1 position a), which is invariant in all Myc proteins, and the histidine opposite it in Max leucine zipper position d'.

FIG. 7 shows the nucleic acid and deduced amino acid sequence of the Mxi2-encoding cDNA (SEQ ID NOS: 3 and 4).

FIG. 8 shows a comparison of Mxi2 protein (SEQ ID NO: 3) with human p38 kinase (SEQ ID NO: 20) and Saccharomyces cerevisiae Hog1 protein (SEQ. ID NO:21. Gaps introduced to optimize alignment are illustrated by periods, identical residues are illustrated by dashes, and stop codons are illustrated by asterisks. Mxi2 contains 17 C-terminal amino acids not found in p38 kinase, and p38 kinase contains 80 residues not found in Mxi2 protein.

DESCRIPTION OF THE PREFERRED EMBODIMENT(S)

We now describe the isolation and characterization of Mxi1 and Mxi2, new human proteins that form heterodimeric complexes with Max. These examples are provided for the purpose of illustrating, not limiting, the invention.

Isolation of Mxi1

Figure 1:
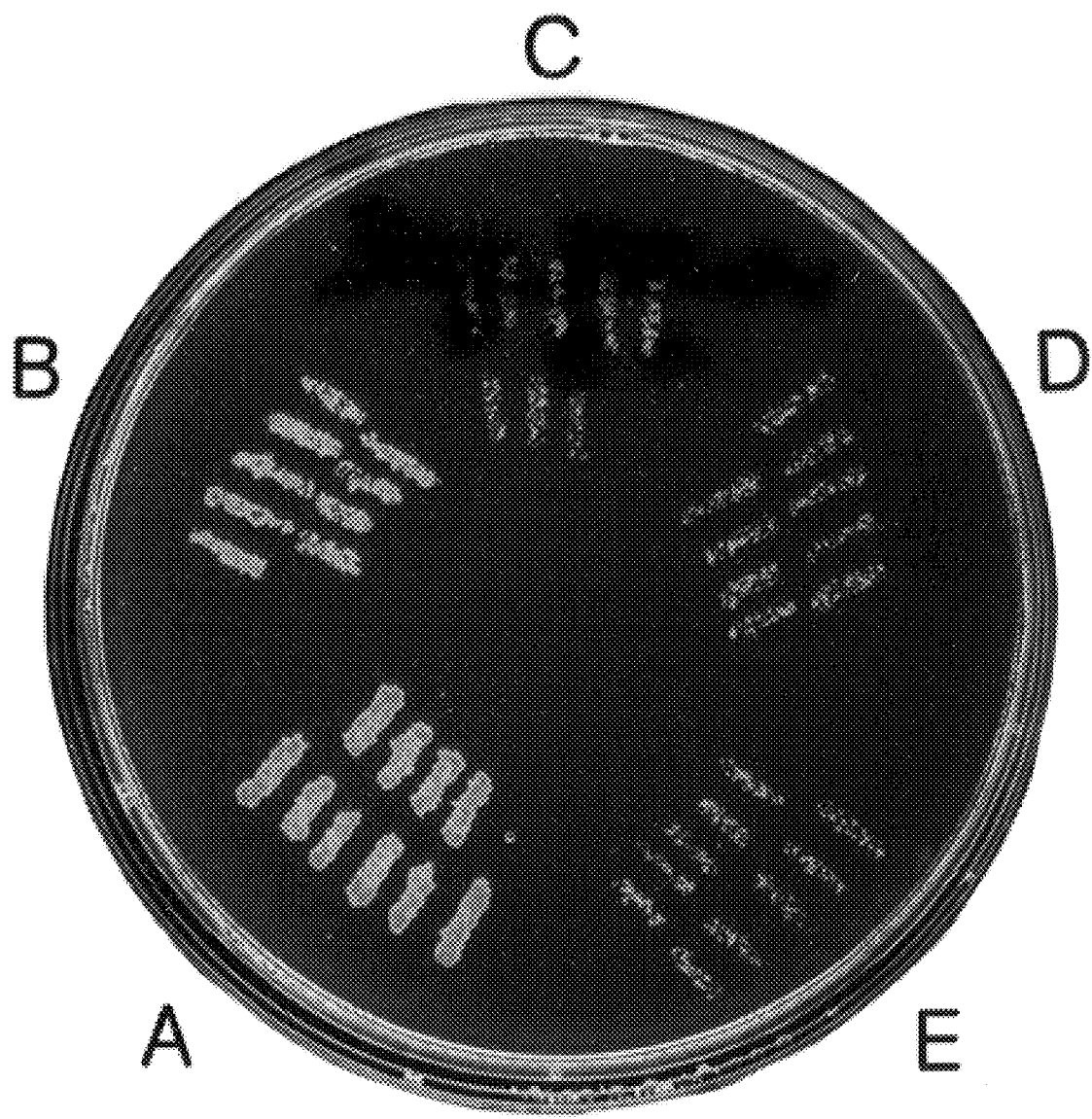
FIG. 1 shows activation by interaction of Mxi1 with different bait proteins. Individual colonies of EGY48 yeast cells that contained tagged Mxi1 (i.e., the invariant activation-tagged moiety of pJG4-5 fused to Mxi1 residues 10–220) and that also contained (A) LexA-Max, (B) LexA-cMyc-Cterm, (C) LexA-Cdc2, (D) LexA-Fus3, or (E) LexA-Bicoid were streaked with toothpicks onto a glucose ura$^-$ his$^-$ trp$^-$ master plate, and then replica plated onto a galactose ura$^-$ his$^-$ trp$^-$ leu$^-$ plate. Interaction results are indicated as activation of the LexAop-LEU2 reporter and as growth in the absence of leucine.

Mxi1 was isolated in an interaction trap system selection for proteins capable of associating with the Max protein (see below). Exactly 100 LEU+ colonies were selected from a population of yeast that derived from 7.5×10⁵ library members; 80 of these colonies also showed unambiguous blue color on Xgal medium (see below). Further analysis by restriction mapping and partial sequencing revealed that many of these (62) encoded human cMyc. The rest, which in the initial screen interacted with Max to different degrees, contained new cDNAs. We selected, for further characterization, that class whose product, after cMyc, gave the strongest activation with the LexA-Max bait. We called the protein encoded by this gene Mxi1 (for Max Interactor 1). We tested the specificity of the Mxi1/Max interaction by testing the ability of Mxi1 to interact with a panel of different baits. Visual inspection of activation of the sensitive LexAop-LEU2 reporter on galactose leu⁻ plates showed that Mxi1 interacted strongly with LexA-Max, detectably with LexA-cMyc-Cterm, but not with LexA-Fus3 or LexA-Bicoid (FIG. 1).

Primary Sequence

The partial Mxi1 open reading frame was sequenced on the library plasmid, which, as expected, was fused in frame to the invariant amino terminal moiety of the library encoded proteins. This cDNA was used to isolate a 2.4 kb cDNA from a commercially available HeLa cDNA library from Stratagene (LaJolla, Calif.); this cDNA was sequenced as well, and the sequence is shown in FIG. 2 (SEQ ID NOS: 1 and 2). The sequence revealed a 220 amino acid open reading frame with 315 5' flanking nucleotides and 1440 3' nucleotides. The Mxi1 open reading frame contained a bHLH-Zip region between amino acids 32–112 that was very similar in sequence to the bHLH-Zip found in Myc family proteins and in Max (FIG. 3a). Compared with human cMyc, 8 out of 12 amino acids in the Mxi1 basic region are identical to those found in Myc, including the arginine at position 44, which contacts the CG core of the cMyc/Max consensus binding site. There is also substantial sequence similarity outside of this region: the Mxi1 HLH is nearly an exact match with the HLH consensus, and, as in Myc family proteins (Beckmann and Kadesch, Genes Dev. 5:1057–1066, 1991), HLH helix II is fused to the leucine zipper so that the hydrophobic heptad repeat in the zipper continues into the C terminus of helix II. Projection of the Mxi1 leucine zipper onto a helical wheel plot suggested that this region might have a favorable ionic interaction with the leucine zipper found in Max (FIG. 3b), but not with one in cMyc.

Outside of the bHLH-Zip, Mxi1 revealed no similarity to known proteins. The sequence did not reveal a classical nuclear localization signal, although arg13, arg14, lys80, and lys82 might constitute a bipartite localization signal (Dingwall and Laskey, Trends Biochem Sci. 18:478–481, 1991). Mxi1 contains an acidic stretch at residues 135 to 180 (15 residues are glutamic or aspartic acid, predicted net charge of −14). The 3' noncoding region contained a stretch that contained substantial similarity to an expressed sequence tag found on a cDNA isolated from human brain (Adams et al., Nature 355:632–634, 1992) (FIG. 2); in particular, positions 1508–1958 contained a 443/450 nucleotide match (with one gap) with an expressed sequence tag (EST02043) from human brain (Adams et al., Nature 355:632–634, 1992).

The GenBank Accession Number for the Mxi1 sequence is L07648.

Association with other Proteins

We tested whether Mxi1 interacted specifically with Max by repeating our initial interaction assays using a series of more closely related baits.

β-galactosidase levels were measured in cultures of yeast strain EGY48 that harbored pJK103, a medium-sensitive LexAop-lacZ reporter, into which plasmids that directed the synthesis of tagged Mxi1 and the listed baits were introduced. Measurements were performed in duplicate on three independent isolates, and the average value is shown in Table 1.

TABLE 1

| | Reporter Expression | | | |
|---|---|---|---|---|
| | Glucose | | Galactose | |
| Bait Protein | Leu | β-galactosidase | Leu | β-galactosidase |
| LexA-c-Myc-Cterm | − | <2 | + | 10 |
| LexA-Max | − | <2 | +++ | 120 |
| LexA-Mxi1 | + | 10 | + | 10 |
| LexA-Hairy | − | <2 | − | <2 |
| LexA-Id | − | <2 | − | <2 |
| LexA-n-Myc-bHLH-Zip | − | <2 | + | 8 |
| LexA-Da | − | <2 | − | <2 |

The results in Table 1 show that Mxi1 interacts strongly with Max, less strongly with the LexA-cMyc-Cterminus, and not at all with baits that contained other bHLH-Zip, bHLH, or b-Zip proteins, including LexA-Nmyc-Cterminus, LexA-Hairy, LexA-Id (HLH), and LexA-Da.

The specificity of the Mxi1/Myc interaction was confirmed by immunoprecipitation experiments with in vitro translated Mxi1 and potential interaction partners (described below). In vitro translated Mxi1 runs on an SDS gel with an apparent molecular weight of 32 kD, higher than the calculated molecular weight of 24.5 kD. Moreover, when Mxi1 is translated together with either form of the Max protein, $Max_{1-151}$ or $Max_{1-160}$, it can be precipitated by anti-Max antibodies, but when it is translated together with cMyc or nMyc, it cannot be precipitated with antisera directed against those proteins.

Site Recognition

Figure 4:
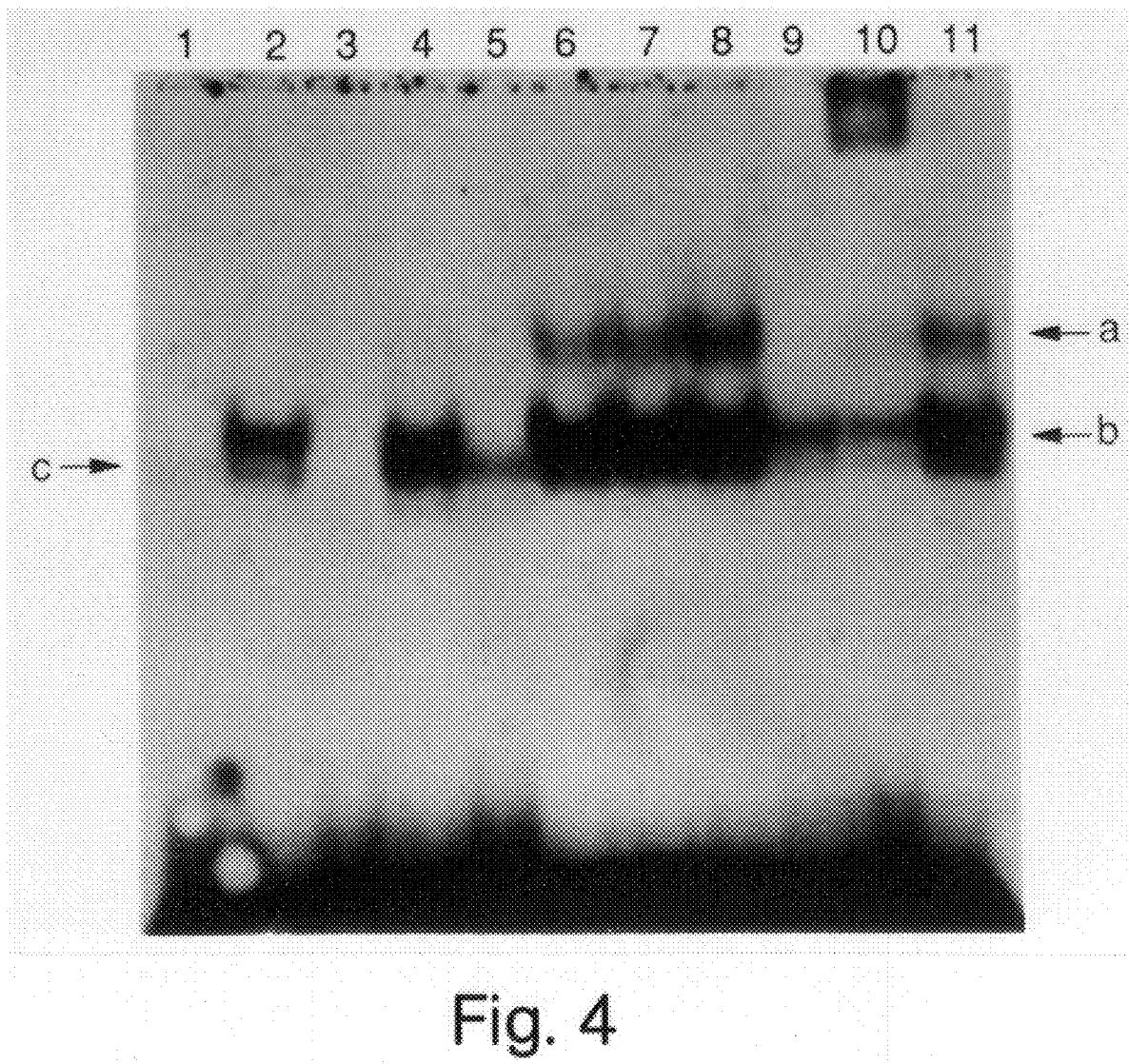
FIG. 4 demonstrates sequence specific binding by Mxi1 and Max. Binding assays used bacterially produced GST-Mxi1, full-length Max, and c-Myc bHLH-Zip (amino acids 342–439). The labeled oligonucleotide contained a consensus Myc-binding site. Binding reactions (20 µl) containing the indicated proteins and other reagents were performed, run on a 5% polyacrylamide gel, and subjected to autoradiography as described (see below), a, b, and c denote specific oligonucleotide-containing complexes. Lane 1, 300 ng of c-Myc bHLH-Zip; lane 2, 10 ng of Max; lane 3, 10 ng of GST-Mxi1; lane 4, 10 ng of Max, 300 ng of c-Myc bHLH-Zip; lane 5, 300 ng of Max, 300 ng of c-Myc bHLH-Zip; lane 6, 10 ng of Max, 10 ng of GST-Mxi1; lane 7, 10 ng of Max, 20 ng of GST-Mxi1: lane 8, 10 ng of Max, 50 ng of GST- Mxi1; lane 9, 10 ng of Max, 50 ng of GST-Mxi1, pretreated with 10 µl of 50% w/v glutathione-Sepharose beads, supernatant loaded on gel; lane 10, 10 ng of Max, 50 ng of GST-Mxi1, 1 µl of anti-Max antiserum; lane 11, 10 ng of Max, 50 ng of GST-Mxi1, 1 µl of control antiserum.

The above results suggest that Mxi1 interacts strongly and specifically with Max. The sequence of the Mxi1 bHLH-Zip region suggested that such Mxi1/Max heterodimers should bind the consensus Myc/Max recognition site. This was tested by assaying the ability of combinations of glutathione S-transferase (GST)-$Mxi1_{1-220}$, purified $Max_{1-151}$, and purified c-Myc bHLH-$Zip_{342-439}$ to retard the electrophoretic mobility of an oligonucleotide that contained the CACGTG Myc-Max consensus site (Halazonetis and Kandil, Science 255:464–466, 1991). These results are shown in FIG. 4. As expected, purified c-Myc bHLH-Zip caused the formation of a very small amount of retarded complex (FIG. 4, lane 1, complex c), purified Max caused the appearance of a larger amount of retarded complex of different mobility (lane 2, complex b), purified GST-Mxi1 did not give detectable amounts of retarded complex (lane 3), which we attribute to its inability to interact with itself (Table 1), and GST-Mxi1 and c-Myc bHLH-Zip did not form appreciable amounts of a new complex (lane 5). However, addition of GST-Mxi1 to Max resulted in the appearance of a complex of altered mobility (complex a, lane 5; the amount of this complex was increased with increasing amounts of GST-Mxi1 (lanes 7 and 8). This complex contained both Mxi1 and Max; treatment of the binding mixes with glutathione-Sepharose removed this complex quantitatively from the binding mix (lane 9), and treatment of the binding reactions with anti-Max antiserum resulted in the disappearance of most of the Mxi1-Max-DNA complex and its apparent supershift to a much less mobile DNA complex (lane 10). These results demonstrate that Mxi1 and Max complexes bind Myc-Max recognition sites.

Transcription Activation by Mxi1

The ability of Mxi1 to stimulate transcription was assayed. Plasmids directing the synthesis of LexA derivatives of Mxi1, Max, and cMyc were introduced into EGY40/pJK103, and β-galactosidase assays were performed on cultures of independent transformants as described below. These results are shown in Table 2.

TABLE 2

| Potential Activator Protein | Reporter Expression (β-gal Units) |
| --- | --- |
| LexA-cMyc | 12 |
| LexA-Max | <2 |
| LexA-Mxi1 | <2 |

The results in Table 2 demonstrate that, unlike cMyc but like Max, Mxi1 is transcriptionally inert in this assay.

Mxi Expression

Figure 5:
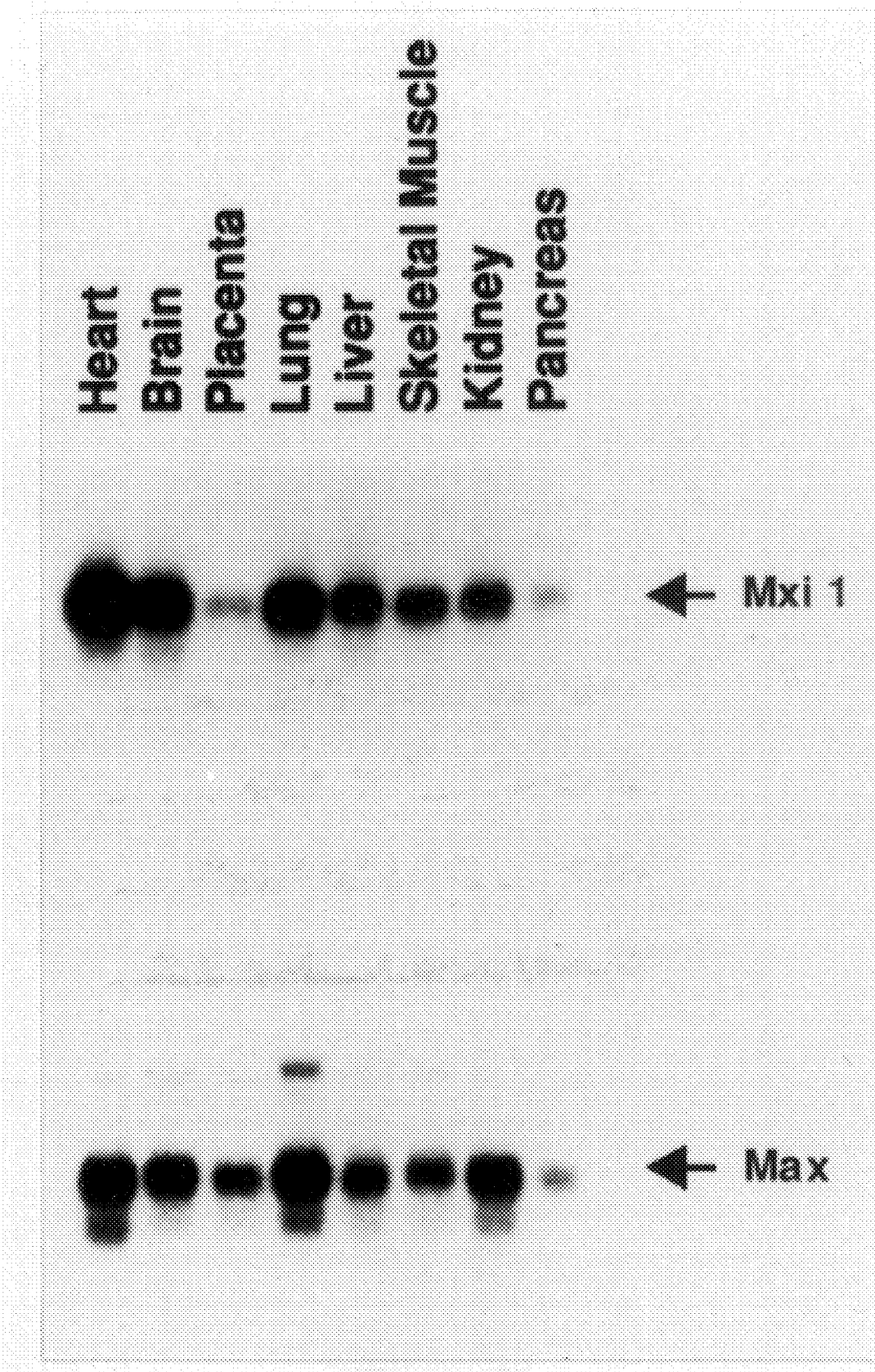
FIG. 5 shows the expression of Mxi1 and Max mRNA in different tissues. mRNA from different human tissues was probed with Mxi1, then stripped and reprobed with Max as described below (experimental procedures). Each lane contains 2 µg of polyA+ mRNA from (1) heart, (2) brain, (3) placenta, (4) lung, (5) liver, (6) skeletal muscle, (7) kidney, and (8) pancreas. Mxi1 mRNA runs with an apparent mobility of 3.2 kb, Max with an apparent mobility of 2 kb.

In order to determine in which tissues Mxi1 was expressed, a Northern blot containing 2 µg of polyA RNA from different human tissues (obtained from Clontech, Palo Alto, Calif.) was probed with Mxi1 and Max. This experiment revealed that Mxi1 mRNA was expressed in every tissue tested, with the highest levels in heart, brain, and lung (FIG. 5). The pattern of Max expression closely mirrors that of Mxi1 (FIG. 5). Northern analysis of Mxi1 mRNA expression in serum-starved and serum-stimulated WI38 human lung fibroblasts revealed that expression of the Mxi1 message was not induced by serum. Analysis of Mxi1 mRNA in synchronized populations of HeLa cells showed that its expression was also invariant through the cell cycle.

Mxi1 expression was next examined during differentiation of cells of the lymphoid lineage. We used such cells for three reasons: first, because down-regulation of Myc mRNA levels occurs upon differentiation; second, because constitutive expression of Myc can block their differentiation; and third, because we reasoned that changes in the differentiation state might affect the expression of other Myc-related messages.

In these experiments, RNA derived from two different premonocytic cell lines, U-937 and HL-60, was utilized. These lines are believed to correspond to different stages of monocytic development; U-937 is thought to be derived from a more determined cell type than HL-60. These lines can be induced to differentiate by a number of agents (reviewed in Harris and Ralph, J. Leukocyte Biol. 37:407–422, 1985); when so treated, U-937 differentiate along the monocytic pathway, while HL-60 differentiate into monocytes or granulocytes depending on the inducing agent. Expression of these messages was measured in myeloid cells for two reasons. First, because constitutive expression of c-Myc can block their differentiation (Freytag, Mol. Cell Biol. 8;1614–1624, 1988; Kume et al., J. Mol. Biol. 202:779–785, 1988); second, because down-regulation of c-Myc mRNA levels occurs during differentiation (Watanabe et al., Biochem. Biophys. Res. Comm. 126:999–1005, 1985; Gunji et al., J. Clin. Invest. 89:954–960, 1992), we thought that changes in the levels of myc-related messages might also occur during their differentiation.

Figure 6:
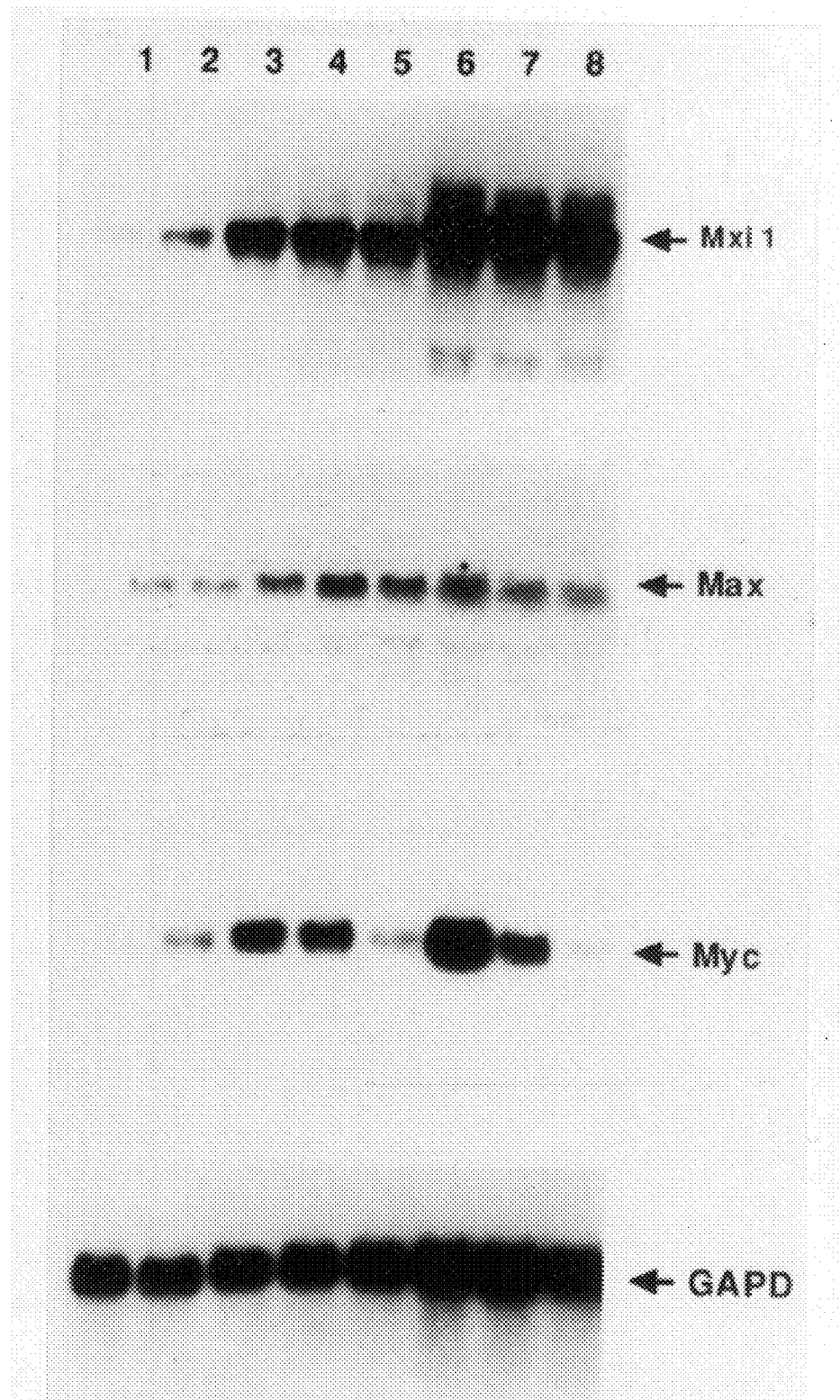
FIG. 6 shows the expression of Mxi1, Max, and Myc mRNA during differentiation. RNA was isolated from U937 and HL60 cells at different times after they were induced to differentiate with TPA (U-937) or retinoic acid (HL-60). 20 µg of RNA from cells from each time point was run on a gel and blotted onto a nylon membrane, which was probed successively with Mxi1, Max, cMyc, and human GAPD as described below (experimental procedures). Lane 1: U937, untreated; Lane 2: U937, 1 hour after TPA induction; Lane 3: U937, 3 hours after TPA induction; Lane 4: U937, 6 hours after TPA induction; Lane 5: U937, 12 hours after TPA induction; Lane 6: HL60, uninduced; Lane 7: HL60, 24 hours after retinoic acid induction; and Lane 8: HL60, 72 hours after retinoic acid induction.

As is shown in FIG. 6, treatment with TPA, the strongest inducer of U-937 differentiation, induces Mxi1 mRNA by a factor of about 20 (lanes 1–5). In order to verify that this induction was a consequence of differentiation, rather than a simple transcriptional response to TPA itself, Mxi1 message was examined in cells that were induced to differentiate with a number of other agents, including DMSO, retinoic acid, vitamin D3, tumor necrosis factor-α, and okadeic acid. Treatment with these agents also induced Mxi1 mRNA expression; the amount of Mxi1 induction by these agents paralleled their potency as inducers of differentiation (as determined by changes in morphology and induction of c-fms message).

In these cells, Max mRNA was low and its expression was not affected by treatment with TPA (FIG. 6). cMyc mRNA, as expected (Gunji et al., J. Clin. Invest. 89:954–960, 1992), was induced briefly, and then returned to a very low level (FIG. 6). By contrast, in HL60 cells, the basal level of Mxi1 and Max mRNA was much higher (lane 6). This level was not elevated in RNA from cells that were induced to differentiate with retinoic acid, although, as expected, the amount of c-myc mRNA was greatly reduced (lanes 7 and 8) (Watanabe et al., Biochem. Biophys. Res. Commun. 126:999–1005, 1985).

The Mxi1 Protein

We used the interaction trap to isolate Mxi1, a protein that interacts specifically with Max. The Mxi1 cDNA is 2400 nucleotides in length. Within it, there is an open reading frame that encodes a 220 amino acid protein, followed by a very large 3' untranslated region. The Mxi1 protein predicted from this open reading frame lacks a conspicuous nuclear localization signal, but contains a putative activation domain at its carboxy terminus and a bHLH-Zip motif at its amino terminus. The sequences of the Mxi1 bHLH-Zip is extremely similar to that of Myc family proteins; the basic region is identical in those residues thought to contact DNA. Helical wheel projections suggest that the Max/Mxi1 interaction may depend on a favorable ionic interaction between the leucine zippers of the two proteins.

We tested the function of Mxi1 in three ways. First, we used the interaction trap to further test the specificity of Mxi1's interaction with Max. We found that Mxi1 interacted very specifically with Max, and not with other related bHLH-Zip, bHLH, and bZIP proteins. We confirmed this result by immunoprecipitation experiments showing that in vitro translated Mxi1 interacted specifically with Max. Second, we performed gel retardation experiments that suggest Max/Mxi1 heterooligomers bind tightly to consensus Myc/Max binding sites. Third, we performed yeast transcription experiments. These experiments suggest that, like Max, Mxi1 is transcriptionally inert.

Finally, in an effort to understand Mxi1 function in vivo, we examined the expression of its mRNA. Mxi1 mRNA is expressed in all tissues, including ones, such as the brain, in which cMyc is not expressed. The cells in many of these tissues are terminally differentiated. To explore whether Mxi1 might be expressed in terminally differentiated cells, we monitored the expression of the mxi mRNA in myeloid cell lines whose c-myc mRNA levels were known to depend on their differentiation state. We found that, in U-937 cells that were provoked to undergo differentiation, the expression of mxi mRNA was strongly elevated at all times after induction, while expression of max and c-myc mRNA was elevated only slightly and at intermediate times. In HL-60 cells, which were derived from less determined cells, basal expression of Mxi1, Max and cMyc was high; when granulocyte differentiation was provoked by induction with retinoic acid, expression of Mxi and Max mRNA was not greatly altered, while, as expected, expression of c-myc mRNA was strongly reduced.

As assayed by interaction trap and gel retardation assays, Mxi1 interacts specifically with Max. The sequence of Mxi1 suggests one possible explanation for this specificity: a favorable ionic interaction between the Mxi1 and Max leucine zippers; ascribing an important function to this interaction seems reasonable given the contribution favorable leucine zipper interactions can make to dimerization of another bHLH-Zip protein, cMyc itself (Halazonetis and Kandil, Proc. Natl. Acad. Sci. USA. 88:6162–6166, 1991). These experiments do not exclude the idea that Mxi1 might be able to form homodimers; if they did, they might be expected to associate with this same site.

We note that the interaction trap reveals a weak association between Mxi1 and Myc. We attribute our ability to detect this association to at least two causes: first, the relatively high intranuclear protein concentrations in this assay ($10^{-6}$M vs. $10^{-10}$M in typical immunoprecipitation experiments), and second, to our use of a sensitive LexAop-LEU2 reporter in the interaction trap system.

The experiments described herein identified four facts about Mxi1 that we believe are likely to be significant: its interaction with Max, its ability when complexed with Max to bind Myc/Max recognition sites, its lack of activation function, and its up-regulation, together with Max, in differentiating lymphoid cells.

These facts suggest that Mxi1 may affect Myc function negatively, in two ways, first by sequestering the Max that Myc needs to bind sites on DNA, and second, by forming inert complexes with Max that compete with transcriptionally active Myc/Max heterodimers for binding sites upstream of genes. According to this view, Mxi1 would normally inhibit Myc-dependent oncogenesis (i.e., act as an antioncoprotein), and, when its synthesis was induced during differentiation, would prevent Myc from activating transcription of its normal target genes. As such, the Mxi polypeptide is likely useful as an anti-cancer therapeutic (i.e., as a polypeptide which promotes differentiation). Its widespread expression in terminally differentiated cell lines (e.g., heart, brain, lung, liver, skeletal muscle, kidney and pancreas) suggests that it may be useful for treating any number of different malignancies. Experiments described herein suggest its particular utility in treating hematopoietic malignancies, such as leukemias or lymphomas.

Moreover, because Mxi expression correlates with differentiation, at least in monocytic lineages, detection of a change in Mxi polypeptide cellular expression may be used as a diagnostic for detecting or monitoring malignant conditions or their treatment.

Mxi1 Fragments

Because Mxi1 likely exerts its effects by interacting with and sequestering cellular Max polypeptides, that portion of Mxi1 which binds Max may be useful in place of the full-length protein, for example, for therapeutic purposes. Such a Max-interacting fragment of Mxi1 preferably includes Mxi1's leucine zipper and may further include one or both of the surrounding helices. Referring to the sequence shown in FIG. 2 (SEQ ID NO: 1), Mxi1 fragments useful in the invention include (but are not limited to) amino acids 91–112 (comprising the Mxi1 leucine zipper) and amino acids 68–112 (comprising the Mxi1 leucine zipper and helix II).

The Mxi2 Protein

A second protein capable of interacting directly or indirectly with Max was isolated in the interaction trap screen described above. This protein was termed Mxi2, for Max Interactor 2. Mxi2 is a new protein kinase of the ERK type. Interaction trap experiments show that it also interacts, with equivalent affinity, with the cMyc oncoprotein itself.

Previous experiments have shown that ERK kinase acts at a site in Myc whose ability to be phosphorylated is necessary for Myc-mediated cell transformation; our experiments are thus consistent with the idea that Mxi2 is the ERK kinase whose action is necessary for Myc-dependent carcinogenesis (Alvarez et al., J. Biol. Chem. 266:15277–15285, 1991).

Characterization of Mxi2 (as described above) indicates that Mxi2 is a 297 residue protein whose sequence clearly identifies it as a member of the ERK protein kinase family (Crews et al., Cell Growth and Differentiation 3:135–142, 1992). The Mxi2 sequence is shown in FIG. 7 (SEQ ID NOS: 3 and 4) Its sequence is homologous to the other members of the ERK kinase family over the catalytic domain. Outside of that domain, Mxi2 exhibits no significant homology to known proteins. Mxi2's divergent regions may endow the protein with its specificity for Myc and Max. There is also some reason to believe that Mxi2 will be the ERK type kinase that kinases cJun (Alvarez et al., 1991, supra); if this is true, then Mxi2 may also may be necessary for Jun/Fos dependent cancers and signal transduction events. In more detail, this protein was isolated and characterized as follows.

We used the interaction trap (Gyuris et al., Cell 75:791–803, 1993), a yeast two-hybrid system (Fields et al., Nature 340:245–246, 1989), to isolate Mxi2, a protein that interacted specifically with Max protein for a HeLa cDNA library (Zervos et al., Cell 72:223–232, 1993). We isolated $7.5 \times 10^5$ colonies that contained individual members of a HeLa cDNA interaction library (Gyuris et al., Cell 75:791–803, 1993) and plated cells from these colonies on selective medium plates at a multiplicity of 10. From these cells we isolated 80 plasmids that interacted with a LexA-Max bait (Zervos et al., Cell 72:223–232, 1993). cDNA inserts from these plasmids fell into three restriction map classes, one of which, composed of a single plasmid, contained the Mxi2 coding sequence. As judged by growth on LEU⁻ medium and blue color on 5-bromo-4-chloro-3-indolylβ-D-galactoside (dependent on the medium strong pJK103 LexAop-LacZ reporter), Mxi2 was the third strongest interactor (after c-Myc and Mxi1), consistent with its low frequency of isolation. Mxi2 was specific for Max protein; in the interaction trap, it did not interact with LexA-Cdc2, LexA-Fus3, or LexA-Bicoid baits but interacted with a bait containing the C terminus of Myc.

FIG. 7 shows the sequence of Mxi2. The 1023-bp cDNA encodes a polypeptide of 297 amino acids with significant sequence similarity to the yeast HOG1 gene product (see FIG. 8), an ERK involved in osmoregulation (Brewster et al., Science 259:1760–1763, 1993). The sequence suggests that Mxi2 is an alternatively spliced form of the recently described human p38 protein kinase (Han et al., Science 265:808–811, 1994). In human cells, p38 kinase is activated by tyrosine and threonine phosphorylation in response to lipopolysaccharide, inflammatory cytokines (tumor necrosis factor, interleukin 1), and environmental stress (Han et al., Science 265:808–811, 1994; Brewster et al., Science 259:1760–1763, 1993). Recently another protein kinase, CSPB1, that is involved in lipopolysaccharide-induced cytokine biosynthesis and is the target of several anti-inflammatory drugs, has been isolated; an alternative spliced form, CSBP2, was shown to be p38 kinase (Lee et al., Nature 372:739–746, 1994).

Figure 9:
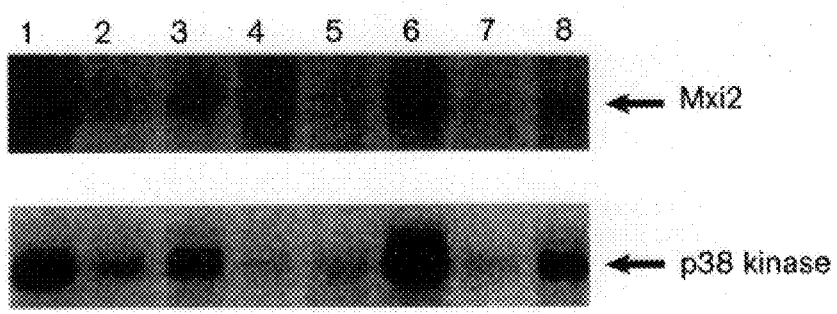
FIG. 9 shows the expression of Mxi2 and p38 mRNA in different human tissues. The Northern blots each contained 2 µg of poly(A)+ RNA per lane. The top blot was probed with an Mxi2-specific probe, and the bottom blot was probed with a p38 kinase-specific probe. Eight different human tissues were analyzed: lane 1, heart; lane 2, brain; lane 3, placenta; lane 4, lung; lane 5, liver; lane 6, skeletal muscle; lane 7, kidney; lane 8, pancreas. Mxi2 protein was expressed at much lower levels than p38 kinase in all tissues examined.

Mxi2 protein is identical in sequence to p38 kinase (Han et al., Science 265:808–811, 1994; Lee et al., Nature 372:739–746, 1994) from amino acids 1–280; Mxi2 contains 17 C terminal amino acids not found in p38 kinase, and p38 kinase contains 80 residues not found in Mxi2 protein (see FIG. 8). Northern analysis of mRNA from different human tissues using probes specific for Mxi2 and p38 kinase revealed that Mxi2 protein is expressed at much lower levels than p38 kinase in all tissues tested (FIG. 9). The size of the mRNA is 4.2–4.4 kb, and the relative distribution of Mxi2 in different human tissues mirror closely the distribution of p38 mRNA, except in heart, where the relative expression of Mxi2 is higher.

Mxi2 protein is the smallest ERK family member identified thus far. It lacks a C-terminal stretch (domain XI) (Hanks et al., Methods Enzymol. 200: 38–62, 1991), present in other protein kinases (FIG. 8). Interestingly, the extreme terminus of Mxi2 (residues 283–297) shows some sequence similarity to residues 292–304 of ERK2 (LTITPHLMDIELVMI vs. LTFNPHKRIEVEQ (SEQ ID NOS: 25 and 26)). In ERK2 these residues lie immediately N-terminal to helices αI and αL16, which follow along back of the molecule (Zhang et al., Nature 367:704–711, 1994). This portion of Mxi2 and ERK2 (but not of p38 kinase) may thus mediate interaction with a common modulatory protein.

Figure 10:
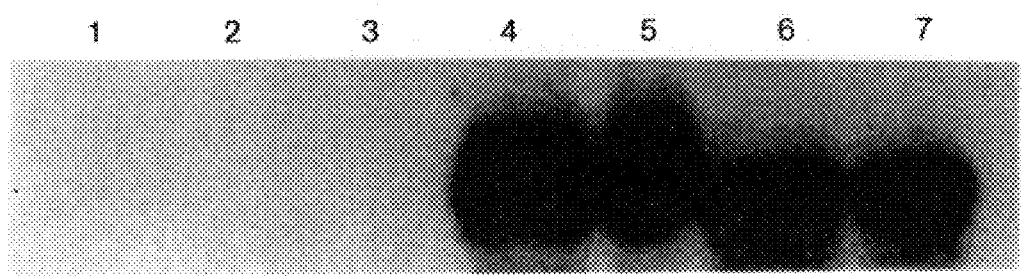
FIG. 10 demonstrates the kinase activity of Mxi2 protein in vitro. The autoradiograph shows transfer of $^{32}PO_4$ to Max protein (lanes 4 and 5) and to myelin basic protein (lanes 6 and 7). Lanes: 1, 5 µg of Max and no Mxi2; 2, Mxi2 from the low-serum COS cells and no Max protein; 3, Mxi2 from serum-stimulated COS cells and no Max protein; 4, Mxi2 from the low-serum COS cells and 5 µg of Max protein; 5, Mxi2 from serum-stimulated COS cells and 5 µg of Max protein; 6, Mxi2 from the low-serum COS cells and 5 µg of myelin basic protein; 7, Mxi2 from serum-stimulated COS cells and 5 µg of myelin basic protein.
Figure 11:
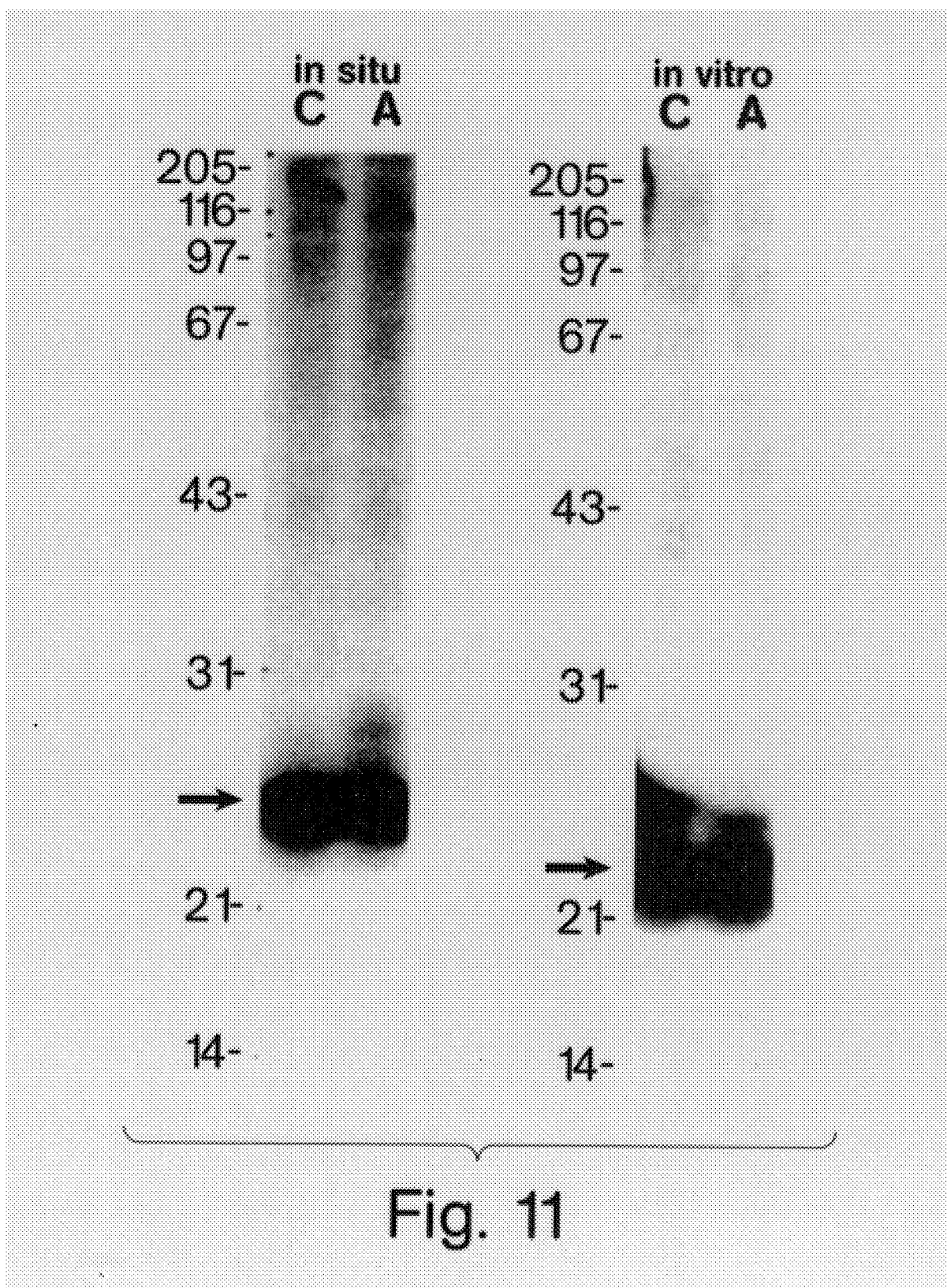
FIG. 11 demonstrates Max phosphorylation by Mxi2 in vitro or in vivo with and without arsenite. SDS/PAGE of HA-Max phosphorylated in situ (left) or bacterially expressed, purified hexahistidine-Max phosphorylated by immunoprecipitated HA-Mxi2 in vitro (right). Arrows show Max phosphorylation in C, control cells; A, arsenite-treated cells. There was no detectable difference in Max phosphorylation between control cells or arsenite-treated cells.

Mxi2 isolated from COS cells transfected with a construction that directs the synthesis of epitope-tagged Mxi2 phosphorylates Max protein in vivo (FIG. 10). It also phosphorylates myelin basic protein, a common nonspecific substrate of many ERK family kinases (FIG. 9). Mxi2 expressed in transfected cells display a strikingly high basal activity toward Max and is equally active at phosphorylating Max when isolated from COS cells that are serum-starved, serum-stimulated, or treated with arsenite which increases p38 activity (Marais et al., Cell 73:381–393, 1993) (FIGS. 10 and 11). We studied Max phosphorylation in vivo in COS cells treated with arsenite. There was no detectable difference in Max phosphorylation between control cells, serum-starved cells, serum-stimulated cells, or arsenite treated cells (FIGS. 10 and 11).

Like Mxi2, p38 isolated from COS cells also phosphorylates Max in vitro; however, it is possible that their relative affinities for their substrates differ; in the yeast two-hybrid system we were unable to detect interaction between a LexA-p38 kinase unit and Max protein. Consistent with this idea is the fact that p38 kinase is expressed in the HeLa interaction cDNA library we used, but Mxi2 was the only kinase that we isolated.

Figure 12:
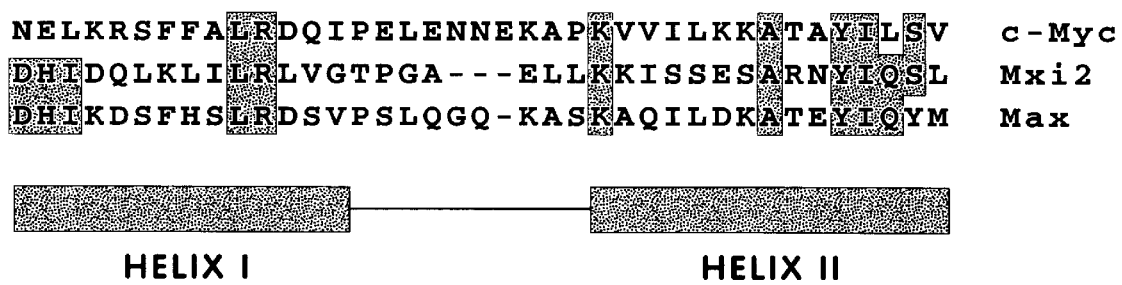
FIG. 12 shows Myc (SEQ ID NO: 22) and Max (SEQ ID NO: 24) HLH sequence and the similarity to a stretch of amino acids in Mxi2 (SEQ ID NO: 23). Residues 227–262 of Mxi2, residues 386–406 of human c-Myc, and residues 28–65 of human Max are shown. Gaps introduced to optimize the alignment are illustrated with dashes; identical residues in corresponding positions are shown by stipling.

In yeast, Mxi2 interacts with LexA-Max bait and also with a LexA-c-Myc bait that lacks the Myc-terminus but contains the C-terminal basic-HLH-leucine zipper region (Zervos et al., Cell 72:223–232, 1993). This fact led us to search for a region in Mxi2 protein that could direct its interaction with a common region in these two proteins. The Mxi2 C terminus (residues 227–262) carries a stretch of amino acids with significant homology to the HLH of both Max and Myc proteins (FIG. 12). Alignment of this stretch of Mxi2 with ERK2 reveals that it lies in a region of ERK2 that contains helices αG, α1L14, and α2L14; residues in αG are involved in substrate recognition (Zhang et al., Nature 367:704–711, 1994). Inspection of this portion of the Mxi2 sequence suggests that it could form two α-helices separated by a GTGPA linker, and it is thus possible that this stretch helps Mxi2 recognize Max protein by directing oligomerization with the Max HLH. It is interesting to note that CSEP1, an alternatively spliced form of p38 kinase (Hanks et al., Methods Enzymol. 200:38–62, 1991), differs from p38 kinase by 25 amino acids in a region that includes the Mxi2 and Max/Myc homology, and it is plausible that this region of CSBPI directs its interaction with a different set of proteins.

Phosphorylation of Max protein by casein kinase II inhibits the DNA-binding activity of Max homodimers but not the Myc/Max heterodimers (Berberich et al., Genes Dev. 6:166–176, 1992). What might be the effect of Max protein phosphorylation by Mxi2? Because Myc protein expression in the absence of growth factors leads to p53-dependent apoptosis (Evan et al., Cell 69:119–128, 1992; Hermeking et al., Science 265:2091–2093, 1994) and because Max protein may well contribute to the function of Myc protein in this process, Mxi2 might activate apoptosis by phosphorylating Max, and it is interesting in this regard that cells transfected with Mxi2 expression constructs show substantial cell death. Max protein does not contain the Pro-Xaa-(Ser/Thr)-Pro or Ser/Thr-Pro motifs recognized by classical ERK (29), raising the possibility that Mxi2 may have a different substrate-recognition site from the other ERKs. Our data are consistent with the hypothesis that Mxi2 has a distinctive proline requirement: Ser/Thr-Xaa-Pro. Indeed, Max protein has two such sites, S40 (Ser-Val-Pro) and S135 (Ser-Glu-Pro). S40 is located in helix I of the Max HLH motif. Because Max can dimerize with itself as well as form heterodimers with Myc, Mxi1, and Mad proteins, phosphorylation at S40 might change its preference for particular oligomeric partners. Alternatively, because the Max protein basic region and helix I form a continuous α-helix that interacts with DNA (Ferre-D'Amare et al., Nature 363:38–46, 1993), phosphorylation of this residue could also affect the ability of Max protein to bind its sites.

These experiments define Mxi2 as another member of the subfamily of the ERK protein kinases, whose members transduce extracellular signals to the nucleus. These proteins include p44 mitogen-activated protein kinase kinase (ERK1) and p42 mitogen-activated protein kinase kinase (ERK2), which phosphorylate transcription factors Elk1/p62$^{TCF}$ (Marais et al., Cell 73:381–393, 1993; Gille et al, Nature, 358:414–417, 1992), and the stress activated protein (SAP) kinase subfamily of ERKs which phosphorylate Jun and transcription factor ATF2 (Kyriakis et al., Nature 369:156–160, 1994; Derijard et al., Cell 76:1025–1037, 1994; Abdel-Hafiz et al., Mol. Endocrinol 6:2079–2089, 1992). By analogy with other ERKs, we view it as likely that Mxi2 will be activated by a mitogen-activated protein kinase/ERK (MEK)-like kinase, in response to some stress signal(s), causing it to phosphorylate Max protein and perhaps other basic-HLH proteins. Recently, two human mitogen-activated protein kinase kinases, MKK3 and SEK1 (MKK4) (Derijard et al., Science 267:682–685, 1995; Yan et al., Nature 372:798–800, 1994), have been cloned. MKK3 kinase can specifically activate p38 kinase, whereas SEK1 kinase activates the stress-activated protein kinases, and possibly p38 kinase as well (Derijard et al., Science 267:682–685, 1995; Yan et al., Nature 372:798–800, 1994); SEK1 kinase, in turn, is a substrate of MEK kinase 1 (Yan et al., Nature 372:798–1800, 1994). Because of the sequence homology, we expect the MEKS to activate Mxi2, supporting the hypothesis that Mxi2 protein is also part of a stress-activated signaling pathway. Phosphorylation of Max protein by activated Mxi2 should result in changes in Max activity, which will modulate the transcription of target genes in response to stress.

Plasmids and Strains

Standard manipulations of *E. coli*, nucleic acids, and yeast were performed essentially as described in Ausubel et al., (*Current Protocols in Molecular Biology*, Greene Wiley-Interscience, New York 1989; Guthrie and Fink, Meth. Enzymol. 194:1–751, 1992). Bacterial strain KC8 (pyrF::Tn5, hsdR, leuB600, trpC9830, lacD74, strA, galK, hisB436) was used for the rescue of yeast plasmids as described (Hoffman and Winston, Gene 57:267–272, 1987). Transformants were collected on Trp-ampicillin plates.

Yeast strain EGY48 (MATa trp1 ura3 his3 LEU2::pLEU2-LexAop6) was constructed as follows. EGY12 (MATa trp1 ura2 LEU2::pLEU2-0 (ΔUASLEU2)) and EGY38 (as above but ::pLEU2-LexAop6) were first constructed using pLEU2-0 and pLEU2-LexAop6. These plasmids were linearized by digestion with ClaI within the LEU2 gene, and the DNA was introduced into U457 (MATa SUP53-a ade2-1 can1-100 ura3-52 trp1-1 [phi+]) by lithium acetate transformation (Ito et al., J. Bacter. 153:163–68, 1983); $ura^+$ colonies, which presumably contained the plasmid DNA integrated into LEU2, were selected. Several of these transformants were grown in YPD. $Ura^-$ cells were selected by plating these cultures on medium that contained 5-FOA (Ausubel et al., supra). Both plasmids carry a TY1 element. For each integration, some of the $ura3^-$ revertants were also $trp1^-$, suggesting that the $URA3^+$ marker was deleted in a homologous recombination event that involved the TY1 sequences on the LEU2 plasmids and the chromosomal TY1 element upstream of SUP53-a (Oliver et al., Nature 357:38–46, 1992). $Trp^-$ colonies from each integration, EGY12 (no LexA operators) and EGY38 (6 operators) were saved. These strains were then mated to GG100-14D (MATα his3 trp1 pho5). The resulting diploids were sporulated, and a number of random (MATα $leu2^-$ $ura3^-$ $trp1^-$ $his3^-$ $GAL^+$) spore products were recovered. EGY40 and EGY48 are products of this cross; EGY40 has no LexA operators, EGY48 has 6.

To make the baits strains, EGY48 was transformed with the reporter pJK103 (Kamens et al., Mol. Cell Biol. 10:2840–2847, 1990), which directs expression of a GAL1-LacZ gene from two high affinity ColE1 LexA operators (Ebina et al., J. Biol. Chem. 258:13258–13261, 1982). This reporter presumably binds 4 LexA dimers; it is about 5 times as sensitive to activation by LexA-containing proteins as is p1840 (Brent and Ptashne, Nature 312:612–615, 1984) although it is still not as responsive as the LexAop-LEU2 reporter in EGY48. Double tranformants were selected on Glucose $Ura^-$ $His^-$ plates.

All plasmids used to express the different baits, were based on pL202P1 (Ruden and Ptashne, Nature 350:250–252, 1991), which carries the $HIS3^+$ marker and a 2μ replicator. All baits contained, at their amino terminus, the LexA DNA binding domain and the C-terminal dimerization domain, which directs efficient operator occupancy by the bait (Golemis and Brent, Mol. Cell Biol. 12:3006–3014, 1992). LexA-Max contains the entire 151 residue form of the human Max protein (Blackwood and Eisenman, Science 251:1211–1217, 1991), LexA-cMyc-Cterm contains the 176 carboxy terminal amino acids of human c-Myc, but lacks the activation domains (Kato et al., Mol. Cell. Biol. 10:5914–5920, 1990. Both were cloned as EcoRI-BamHI fragments into pL202P1 after standard PCR amplification. (Vent Polymerase, New England Biolabs, Beverly, Mass.); in these constructions, no amino acids were introduced into the junction of these fusion proteins. LexA-Fus3 and LexA-Cln3, which contain the entire yeast FUS3 protein (Elion, Cell 60:649:664, 1990) and the entire CLN3 protein (Cross, Mol. Cell Biol. 8:4675–4684, 1988; Nase et al., EMBO J. 7:4335–4346, 1988) respectively, were constructed in the same manner, except that they were cloned as a BamHI fragment. These plasmids contained five amino acids (glu phe pro gly ile) inserted between lexA and the second amino acid of either Fus3 or Cln3. LexA-Bicoid contained residues 2–160 of the Drosophila bicoid gene product (Golemis and Brent, Mol. Cell Biol. 12:3006–3014, 1992), and LexA-nMyc contained the C-terminal 102 amino acids of the nMyc protein, including the bHLH-Zip. LexA-Id contained amino acids 64–133 of the human Id protein, LexA-Hairy contained the full length Drosophila hairy product, and LexA-Da contained residues 485–701 of the daughterless product.

Library-encoded proteins were expressed from pJG4–5, a member of a series of expression plasmids designed to be used in the interaction trap and to facilitate analysis of isolated proteins. These plasmids all carried the 2μ replicator to ensure high copy number in yeast, and the TRP1 marker. pJG4-5 was designed to possess the following features: a galactose-inducible promoter to allow conditional expression of the library proteins, an epitope tag to facilitate their detection, a nuclear localization signal to maximize their intranuclear concentration in order to increase the sensitivity of the selection, and a weak acid blob activation domain (Ma and Ptashne, Cell 51:113–119, 1987). This weak activation domain was chosen for two reasons: (i) because its activity is not subject to known regulation by yeast proteins as is the major GAL4 activation domain, and, more importantly, (ii) because it avoids the toxicity due to squelching or other mechanisms characteristic of strong activation domains (like GAL4) (Gill and Ptashne, Nature 334:721–724, 1988, Berger et al., Cell 70:251–265, 1992) which very likely restrict the number or type of interacting proteins recovered.

pJG4-5 was constructed as follows. An "expression cassette" containing the GAL1 promoter and the ADH1 terminator and a 345 nt insert that encoded a 107 amino acid moiety was inserted into pJG4-0, a plasmid that carries the TRP1 gene, the 2μ replicator, the pUC13 replication origin, and the ampicillin resistance gene. The pJG4-5 expression cassette directed the synthesis of fusion proteins, each of which carried at the amino terminus, amino to carboxy terminal, an ATG, an SV40 nuclear localization sequence (PPKKKRKVA) (SEQ ID NO: 5) (Kalderon et al., Cell 39:499–509, 1984), the B42 acid blob transcriptional activation domain (Ma and Ptashne, Cell 51:113–119, 1987) and the HA1 epitope tag (YPYDVPDYA) (SEQ ID NO: 6) (Green et al., Cell 28:477–487, 1980).

Library Construction

The activation-tagged yeast cDNA expression library was made from RNA isolated from serum grown, proliferating HeLa cells that were grown on plates to 70% confluence. Total RNA was extracted as described in Chomczynski and Sacchi (Anal. Biochem. 162:156–159, 1987), and $polyA^+$ mRNA was purified on an oligodT-cellulose column. cDNA synthesis was performed according to Gubler and Hoffman (Gene 25:263–269, 1983) as modified by Huse and Hansen (Strategies 1:1–3, 1988) using a linker primer that contained, 5' to 3', an 18 nt polydT tract, an XhoI site, and a 25 nt long GA rich sequence to protect the XhoI site. To protect any internal XhoI sites, the first strand was synthesized in the presence of 5'-methyl-CTP (instead of CTP) with an RNAseH defective version of the Moloney virus reverse transcriptase (Superscript, BRL, Grand Island, N.Y.). For second strand synthesis, the mRNA/cDNA hybrid was treated with RNAseH and E. Coli DNA polymerase I, and the resulting ends were made flush by sequential treatment with Klenow, Mung Bean exonuclease, and Klenow onto which EcoRI adaptors:

5' AATTCGGCACGAGGCG 3' (SEQ ID NO: 7)

3' GCCGTGCTCCGC 5' (SEQ ID NO: 8)

were ligated, and the cDNA was digested with XhoI. This DNA was further purified on a Sephacryl S-400 spin column in order to remove excess adaptor sequences, and fractionated on a 5–20% KoAc gradient. Fractions containing >700 bp cDNAs were collected, and approximately 1/5 of the cDNA was ligated into EcoRI- and XhoI-digested pJG4-5.

This ligation mixture was introduced into *E. coli* SURE cells by electrophoration (Gene-Pulser, Bio-Rad, Hercules, Calif.) according to the manufacturer's instructions. 9.6×10$^6$ primary transformants were collected by scraping LB ampicillin plates. Colonies were pooled and grown in 6 liters of LB medium overnight (approximately three generations), and plasmid DNA was purified sequentially by standard techniques on two CsCl gradients. Digestion of transformants of individual library members with EcoR1 and XhoI revealed that >90% of the library members contained a cDNA insert whose typical size ranged between 1 kb–2 kb. Western blots of individual yeast transformants using the anti-hemagglutinin monoclonal antibody suggested that between ¼ and ⅓ of the members expressed fusion proteins.

Interaction Trap Screening

Yeast strain EGY48 was transformed with JK103 and a LexA-Max expression plasmid (termed PL-Max), and transformants were maintained under Ura and His selection. This strain was then transformed with the library according to the procedure described by Ito et al. (J. Bacter. 153:163–168, 1983), except that the cells were grown to a higher OD as described in Schiestl and Gietz (Curr. Genet 16:339–346, 1989) and single stranded carrier DNA was included in the transformation mix, also as described in Schiestl and Gietz (Curr. Genet 16:339–346, 1989). 750,000 primary yeast transformants were selected on Ura$^-$ His$^-$ Trp/$^-$/glucose plates, scraped, pooled and stored at –70°. Plating efficiency was determined on ura$^-$his$^-$trp$^-$/Galactose plates, and five colony forming units/original transformant (i.e., approximately four million cells) were plated on Ura$^-$ His$^-$ Trp$^-$ Leu-/Galactose plates. Three days later, colonies appeared; these were restreaked and tested on Ura$^-$ His$^-$ Trp$^-$ Xgal/. Glucose and Ura$^-$ His$^-$ Trp$^-$ Xgal/Galactose plates. Plasmids from colonies that grew on leu$^-$ plates and turned blue on X-gal medium were isolated as described by Hoffman and Winston (1987; supra) and introduced into KC8 cells by electrophoration. Library plasmids was selected by growing the KC8 transformed cells on 1XA glucose Trp$^-$ Amp plates that contained uracil, histidine, leucine, and thiamine (Miller, Experiments in Molecular Genetics, Cold Spring Harbor Laboratory, New York, 1972).

cDNAs were first analyzed by restriction mapping using EcoRI, XhoI, and AluI enzymes and sorted into classes depending on their restriction map pattern. As least one representative cDNA from each class was partially sequenced by the dideoxy method using modified T7 DNA polymerase and a commercially available kit from US Biochemical, (Cleveland, Ohio). The full length cDNA clone for Mxi1 was isolated from a HeLa cDNA library in lambda ZapII (Stratagene, LaJolla, Calif.). One and a half million clones were screened using standard techniques (Ausubel et al., 1987; supra). Three positive clones were isolated, of which the longest contained a cDNA insert of 2.4 kb. Following phagemid rescue, the cDNA was completely sequenced by standard techniques using collapsed supercoiled DNA as template.

DNA-Binding Assays

Gel retardation DNA binding assays were performed essentially as described in Papoulas et al., (J. Biol. Chem. 267:10470–10480, 1992). Purified Max and c-Myc bHLH-Zip (which contained residues 342–439 of human c-Myc) were made from recombinant *E. coli* by standard techniques. GST-Mxi1 was made as follows: a fragment that contained the entire coding sequence of Mxi1 was amplified using polymerase chain reaction, subcloned into pGEX-2T (Pharmacia), and transformed into DH5α cells. The fusion protein was induced and isolated as described (Smith and Corcoran, *Current Protocols in Molecular Biology*, Ausubel et al., eds., Greene Publishing and Wiley-Interscience, New York, 1989). A double-stranded oligonucleotide, 5'-GGAAGCAGACCACGTGGTCTGCTTCC-3' (SEQ ID NO: 9), that contained the CACGTG (SEQ ID NO: 10) consensus site was used. Approximately 0.5 μg of oligonucleotide was end labeled with [γ-$^{32}$P] ATP. Binding assays contained the indicated concentrations of purified Max, c-Myc bHLH-Zip, GST-Mxi1, and 0.5 ng of the labeled DNA probe. Assays were performed in a volume of 20 μl, so that the concentration of binding site was 2.5×10$^{-10}$M, the concentration of GST-Mxi1 ranged from 3×10$^{-9}$M (1 μl of Mxi1 in the binding reaction) to 1.5×10$^{-8}$M (5 μl in the binding reaction), the concentration of Max was typically 5×10$^{-9}$, and the concentration of c-Myc bHLH-Zip, which had been purified after renaturation after guanidium treatment of an insoluble protein pellet, was 2.5×10$^{-7}$M. In these assays, the poly(dI-dC) often used as a nonspecific competitor was substituted with 200 ng (1200 X molar excess over labeled oligonucleotide) of a nonspecific single-stranded oligonucleotide (5'-GTAATGCATCCAGTTC-3') (SEQ ID NO: 11) (as in Halazonetis and Kandil, Proc. Natl. Acad. Sci. USA. 88:6162–6166, 1991). Binding was allowed to proceed for 20 min at room temperature in reaction buffer that contained 10 mM Tris (pH 7.4), 80 mM NaCl, 1 mM dithiothreitol, 5% glycerol. Where indicated, 1 μl of either control or anti-Max anterserum was added to the reactions. Binding mixtures were run on a 5% polyacrylamide gel (29:1, acrylamide: bisacrylamide) that contained 0.5×TBE buffer with 0.01% NP-40, with running buffer that contained 0.5×TBE and 0.05% NP-40, after which gels were dried and autoradiographed.

RNA Isolation and Northern Blot Analysis mRNA from differentiating U937 and HL60 cells was prepared by standard techniques. Cells were grown in RPMI 1640 containing 10% (for U937) or 15% (for HL60) heat inactivated fetal bovine serum, 100 units/ml penicillin, 100 μg/ml streptomycin, and 2 mM L-glutamine. U937 cells were treated with 32 nM TPA (Sigma, St. Louis, Mo.) for various times. Total RNA was isolated using the guanidine thiocyanate-cesium chloride method (Chirgwin et al., Biochemistry 18:5294–5304, 1979). 20 μg of RNA from each time point was analyzed by electrophoresis in 1% agarose-formaldehyde gels and transferred to nylon membranes (Zeta-Probe, Biorad, Hercules, Calif.), UV crosslinked, and hybridized as described (Ausubel et al., 1989; supra) to the following $^{32}$P-labeled DNA probes: (a) a 420 bp XhoI-XhoI fragment from pTZ8 corresponding to nucleotides 550 to 970 of Mxi1; (b) a 460 bp EcoR1-BamHI fragment from plasmid pSHmax carrying the full length coding sequence of Max; (c) a 1350 bp EcoR1-BamHI fragment from pSHmyc that contained the human cMyc coding sequence; and (d) a 1268 bp Pst1-Pst1 fragment that carried the full length human glyceraldehyde-phosphate-dehydrogenase (GAPD) coding sequence (Tokunaga et al., Cancer Res. 47:5616–5618, 1987).

Isolation of Mxi2

An interactor hunt from a HeLa library with strain EGY48/pJK103 that contained a LexA-Max bait was conducted as described (Zervos et al., Cell 72:223–232, 1993). One transformant, as judged by transcription phenotypes, contained a fused protein that interacted with Max more weakly than fusion proteins that contained Mxi1 and c-Myc. Plasmid pJG-29 was rescued from these cells into KC8 by electroporation. Both strands of the entire EcoRI-Xho I insert were sequenced.

Mxi2 Expression in Mammalian Cells and Kinase Activity

The following primers were used to PCR amplify the Mxi2 coding sequence from pJG-29: 5'-AGCTACTCTAGAGATGTCTCAGGAGAGGCCCAC-3' and 5'-AAGGAAAA-AAGCGGCCGCAATTTATATCATAACCAATTC-3'. (SEQ ID NOS: 27 and 28). The PCR product was cut with Not I and Xba I and introduced into the pMT3 expression vector (Grove et al., Biochemistry 32:7727–7738, 1993) to create pMT3-Mxi2, which directs the synthesis of an Mxi2 protein that contains a hemagglutin (HA) epitope tag at its N terminus. pMT3-Mxi2 was transfected into 70–80% subcofluent COS cells with Lipofectamine (GIBCO/BRL) according to the manufacturer's instructions. Sixteen micrograms of plasmid was used per 100-mm dish. Two days after transfection, the cells were spilt 1:3 and placed into low serum (0.1% bovine calf serum/Dulbecco's modified Eagle's medium). After 48 hours, the cells were placed into Dulbecco's modified Eagle's medium that contained either 20% bovine calf serum (serum stimulated) or 0.1% bovine calf serum (serum deprived). Protein extracts from transfected COS cells were prepared essentially as described (Grove et al., Biochemistry 32:7727–7738, 1993), and Mxi2-HA protein was purified by using the 12CA5 anti-HA antibody and Sepharose coupled to recombinant *Staphylococcus aureus* protein G (Pharmacia). The kinase activity of Mxi2 was monitored by mixing this protein with either bacterially produced histidine-tagged Max protein (Zervos et al., Cell 72:223–232, 1993), or myelin basic protein and $[\gamma\text{-}^{32}P]ATP$ as described (Grove et al., Biochemistry 32:7727–7738, 1993).

Mxi2 In Vivo Labelling

COS cells were transfected with pMT3-Max or pMT3-Mxi2, which encode HA-tagged constructs of the cognate proteins. Cells transfected with Max construct were labelled with $^{32}P$-labelled $H_3PO_4$ (1 mCi/ml; 1 Ci=37 GBq) for 2 hours. Half of the cells were treated with arsenite as described (Rouse et al., Cell 78:1027–1034, 1994). HA-Max or HA-Mxi2 were immunoprecipitated with anti-HA antibody, and in vivo phosphorylation of purified, bacterially expressed hexanistidine-Max was done using described techniques.

Mxi2 Northern Blot Analysis

The following Mxi2-specific primers were used to amplify a DNA probe: $5''\text{-}^{881}$TGGGTAAGT-TGACCATATATC$^{902}$-3' and $5'\text{-}^{992}$CAACTAATGGTACT-TTATTT$^{973}$-3' (SEQ ID NOS:29 and 30). The 111-bp DNA fragment was $P^{32}$ labelled by using the same PCR primers in a modified Klenow reaction. For the p38 the following primers were used to PCR a p38-specific fragment (Boyle et al., Methods Enzymol. 201:110–152, 1991): $5'\text{-}^{1200}$TGGCTGTCGACTTGCTGGAGAAGAT$^{1225}$-3' and $5'\text{-}^{1529}$GGCACTTGAATAATATTTGGAGAGT$^{1504}$-3' (SEQ ID NOS: 31 and 32). The 329-bp fragment was $^{32}P$-labelled by using random primers (Prime-it II, Stratagene). A human multiple-tissue Northern blot (Clontech) was probed for Mxi2 and p38 kinase expression as described (Zervos et al., Cell 72:223–232, 1993).

Polypeptide Expression

In general, polypeptides according to the invention may be produced by transformation of a suitable host cell with all or part of an Mxi-encoding cDNA fragment (e.g., the cDNAs described above) in a suitable expression vehicle.

Those skilled in the field of molecular biology will understand that any of a wide variety of expression systems may be used to provide the recombinant protein. The precise host cell used is not critical to the invention. The Mxi polypeptide may be produced in a prokaryotic host (e.g., *E. coli*) or in a eukaryotic host (e.g., *Saccharomyces cerevisiae* or mammalian cells, e.g., COS 1, NIH 3T3, or HeLa cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding an Mxi polypeptide would be inserted into the pMAMneo vector in an orientation designed to allow expression. The recombinant Mxi protein would be isolated as described below. Other preferable host cells which may be used in conjunction with the pMAMneo expression vehicle include COS cells and CHO cells (ATCC Accession Nos. CRL 1650 and CCL 61, respectively).

Alternatively, an Mxi polypeptide is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the Mxi polypeptide is cloned into an expression vector which includes the dihydrofolate reductase (DHFR) gene. Integration of the plasmid and, therefore, the Mxi-encoding gene into the host cell chromosome is selected for by inclusion of 0.01–300 $\mu M$ methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification.

Once the recombinant Mxi protein is expressed, it is isolated, e.g., using affinity chromatography. In one example, an anti-Mxi antibody (e.g., produced as described herein) may be attached to a column and used to isolate the Mxi polypeptide. Lysis and fractionation of Mxi-harboring cells prior to affinity chromatography may be performed by standard methods (see, e.g., Ausubel et al., supra). Alternatively, an Mxi fusion protein, for example, an Mxi-maltose binding protein, an Mxi-β-galactosidase, or an Mxi-trpE fusion protein, may be constructed and used for isolation of Mxi protein (see, e.g., Ausubel et al., supra; New England Biolabs, Beverly, Me.).

Once isolated, the recombinant protein can, if desired, be further purified, e.g., by high performance liquid chromatography (see, e.g., Fisher, *Laboratory Techniques In Bio-*

*chemistry And Molecular Biology*, eds., Work and Burdon, Elsevier, 1980).

Polypeptides of the invention, particularly short Mxi fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful Mxi fragments or analogs (described below).

Anti-Mxi Antibodies

A human Mxi protein (or immunogenic fragments or analogues) may be used to raise antibodies useful in the invention; such polypeptides may be produced by recombinant or peptide synthetic techniques (see, e.g., *Solid Phase Peptide Synthesis*, supra; Ausubel et al., supra). The peptides may be coupled to a carrier protein, such as KLH as described in Ausubel et al, supra. The KLH-peptide is mixed with Freund's adjuvant and injected into guinea pigs, rats, or preferably rabbits. Antibodies may be purified by peptide antigen affinity chromatography.

Monoclonal antibodies may be prepared using the Mxi polypeptides described above and standard hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific Mxi recognition by Western blot or immunoprecipitation analysis (by the methods described herein or in Ausubel et al., supra). Antibodies which specifically recognize a Mxi polypeptide are considered to be useful in the invention; such antibodies may be used, e.g., in an immunoassay to monitor the level of Mxi produced by a mammal.

Therapy

The Mxi1 polypeptide of the invention has been shown to interact with key regulators of human cell division, and its expression has been shown to correlate with cell differentiation. In addition, expression of Mxi1 in a wide variety of terminally differentiated tissues suggests a potentially general mechanism for its action. For these reasons, Mxi1 polypeptides present themselves as good candidates for anti-cancer therapeutics. Preferably, such a therapeutic is delivered as a sense or antisense RNA product, for example, by expression from a retroviral vector delivered, for example, to the bone marrow. General methods for introducing recombinant genes into, e.g., human cells for gene therapy are described in Miller (Human Gene Therapy 1:5–14, 1990); Friedman (Science 244:1275–1282, 1989); Eglitis and Anderson (BioTechniques 6:608–614, 1988); Tolstoshev and Anderson (Current Opinion in Biotechnology 1:55–61, 1990); Cornetta et al. (Nucleic Acid Research and Molecular Biology 36:311–322, 1987); Anderson (Science 226:401–409, 1984); Moen (Blood Cells 17:407–416, 1991); and Miller and Rosman (Biotechniques 7:980–990, 1989). Retroviral vectors are particularly well developed and have been used in a clinical setting (see, for example, Rosenberg et al., N. Engl. J. Med. 323:370, 1990). Alternatively, Mxi1 may be delivered locally, for example, directly to tumor cells, e.g., by retroviral transfer. As described above, for therapeutic purposes, full-length Mxi1 or, if desired, Max-interacting fragments of Mxi1 (e.g., fragments which include amino acids 91–112 or amino acids 68–112 of FIG. 2) may be utilized. Mxi1 gene therapy may also be combined with more traditional cancer therapies such as surgery, radiation, or chemotherapy.

Cancer Drug Screening

A cloned Mxi gene (e.g., Mxi1 or Mxi2) and, for example, the yeast interaction trap system described herein, may be used for the straightforward and inexpensive screening of a large number of drugs for those which alter the interaction between the Mxi protein and Max, and thus which are useful as cancer therapeutics. Drugs which increase Max:Mxi interaction would increase reporter gene expression in the interaction trap system, and conversely drugs which decrease Max:Mxi interaction would decrease reporter gene expression.

Alternatively, alterations in any Mxi phenotype may be assayed by any conventional assay which reflects an in vitro or in vivo Mxi activity. In one particular example, anti-cancer therapeutics may be identified using standard in vitro kinase assays and measuring biochemical changes in Mxi2's kinase activity.

Drugs identified by any of the above assays may be tested at a second level for efficacy in animal models, and drugs shown to be effective (for example, drugs which inhibit in vivo tumor formation or progression) may be used as anticancer therapeutics in humans according to their normal dosage and route of administration.

Detection of A Malignant Condition

Mxi polypeptides (e.g., Mxi1 or Mxi2) may also find diagnostic use in the detection or monitoring of cancerous conditions. For example, because Mxi1 expression is correlated with a differentiated cell state, a change in the level of Mxi production (e.g., a decrease in Mxi1 production) may indicate a malignant or pre-malignant condition. In general, levels of Mxi expression may be assayed by any standard technique. For example, Mxi expression may be monitored in a biological sample (e.g., a biopsy) by standard Northern blot analysis or may be aided by PCR (see, e.g., Ausubel et al., supra; *PCR Technology: Principles and Applications for DNA Amplification*, ed., H. A. Ehrlich, Stockton Press, N.Y.). Diagnostic techniques are enabled by the provision of Mxi sequences (e.g., those in FIGS. 2 and 7; SEQ ID NOS: 1 and 3).

Alternatively, immunoassays may be used to detect Mxi protein in a biological sample. Mxi-specific polyclonal, or preferably monoclonal, antibodies (produced as described above) may be used in any standard immunoassay format (e.g., ELISA, Western blot, or RIA assay) to measure Mxi polypeptide levels; again comparison would be to wild type Mxi levels, and a change (e.g., a decrease) in Mxi production would be indicative of a malignant or pre-malignant condition. Examples of immunoassays are described, e.g., in Ausubel et al., supra. Immunohistochemical techniques may also be utilized for Mxi detection. For example, a tissue sample may be obtained from a patient, and a section stained for the presence of Mxi using an anti-Mxi antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

The Mxi polypeptide is also useful for identifying that compartment of a mammalian cell where important cell division control functions occur. Antibodies specific for Mxi may be produced as described above. The normal subcellular location of the protein is then determined either in situ or using fractionated cells by any standard immunological or immunohistochemical procedure (see, e.g., Ausubel et al., supra; Bancroft and Stevens, *Theory and Practice of Histological Techniques*, Churchill Livingstone, 1982).

The methods of the instant invention may be used to reduce or diagnose the disorders described herein in any mammal, for example, humans, domestic pets, or livestock. Where a non-human mammal is treated, the Mxi polypeptide or the antibody employed is preferably specific for that species.

Other Embodiments

In other embodiments, the invention includes any protein which is substantially homologous to a human Mxi polypeptide (FIGS. 2 and 7, SEQ ID NOS: 1–4); such homologs include other substantially pure naturally occurring mammalian Mxi proteins as well as allelic variations; natural mutants; induced mutants; proteins encoded by DNA that hybridizes to the Mxi sequences of FIGS. 2 and 7 under high stringency conditions or low stringency conditions (e.g., washing at 2×SSC at 400° C. with a probe length of at least 40 nucleotides); and polypeptides or proteins specifically bound by antisera directed to a Mxi polypeptide, especially by antisera to the active site or to the Max binding domain of an Mxi protein. The term also includes chimeric polypeptides that include an Mxi fragment.

The invention further includes analogs of any naturally occurring Mxi polypeptide. Analogs can differ from the naturally occurring Mxi protein by amino acid sequence differences, by post-translational modifications, or by both. Analogs of the invention will generally exhibit at least 70%, more preferably 80%, even more preferably 90%, and most preferably 95% or even 99%, homology with all or part of a naturally occurring Mxi sequence. The length of comparison sequences will be at least 8 amino acid residues, preferably at least 24 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally occurring Mxi polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, hereby incorporated by reference; or Ausubel et al., supra, hereby incorporated by reference). Also included are cyclized peptides molecules and analogs which contain residues other than L-amino acids, e.g., D-amino acids or non-naturally occurring or synthetic amino acids, e.g., β or γ amino acids.

In addition to full-length polypeptides, the invention also includes Mxi polypeptide fragments. As used herein, the term "fragment" means at least 10 contiguous amino acids, preferably at least 30 contiguous amino acids, more preferably at least 50 contiguous amino acids, and most preferably at least 60 to 80 or more contiguous amino acids. Fragments of Mxi can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which exhibit biological activity (for example, the ability to interfere with mammalian cell division as assayed herein). Preferably, an Mxi polypeptide, fragment, or analog exhibits at least 10%, more preferably 30%, and most preferably, 70% or more of the biological activity of a full length naturally occurring Mxi polypeptide.

Other embodiments are within the following claims.

We claim:

1. A method of detecting a malignant cell in a biological sample, said method comprising measuring Mxi1 gene expression in said sample by assaying the level of Mxi1 RNA, a decrease in Mxi1 expression relative to a wild-type sample being indicative of the presence of said malignant cell.

2. A method of detecting a malignant cell in a biological sample, said method comprising measuring Mxi1 gene expression in said sample by assaying the level of Mxi1 protein, a decrease in Mxi1 expression relative to a wild-type sample being indicative of the presence of said malignant cell.

3. The method of claim 1 or 2, wherein said Mxi1 is human Mxi1.

4. The method of claim 1 or 2, wherein said biological sample comprises a monocytic cell.

5. The method of claim 1 or 2, wherein said biological sample comprises a cell chosen from the group of tissues consisting of heart, brain, lung, liver, skeletal muscle, kidney, and pancreas.

6. A method of detecting a malignant cell in a biological sample, said method comprising measuring Mxi2 gene expression in said sample by assaying the level of Mxi2 RNA, an increase in Mxi2 expression relative to a wild-type sample being indicative of the presence of said malignant cell.

7. A method of detecting a malignant cell in a biological sample, said method comprising measuring Mxi2 gene expression in said sample by assaying the level of Mxi2 protein, an increase in Mxi2 expression relative to a wild-type sample being indicative of the presence of said malignant cell.

8. The method of claim 29 or 37, wherein said Mxi2 is human Mxi2.

* * * * *

UNITED STATES PATENT AND TRADEMARK OFFICE
CERTIFICATE OF CORRECTION

PATENT NO. : 6,017,692
DATED : January 25, 2000
INVENTOR(S) : Roger Brent et al.

It is certified that error appears in the above-identified patent and that said Letters Patent is hereby corrected as shown below:

Column 1,
Line 29, replace "72" with -- 12 --;
Line 36, remove "(4)";

Column 2,
Line 17, remove "15";

Column 8,
Line 46, replace "1991" with -- 1992 --;

Column 12,
Line 17, replace "may also may be" with -- may also be --;

Column 14,
Line 5, replace "2093" with -- 2096 --;
Line 51, replace "1800" with -- 800 --;

Column 17,
Line 26, replace "Trp/⁻/glucose" with -- Trp⁻/glucose --;
Line 37, replace "was" with -- were --;
Line 52, replace "1987" with -- 1989 --;

Column 18,
Line 12, replace "$_{10}$M" wiht -- $^{10}$M --;

Column 20,
Line 64, replace "Me." with -- Mass. --

Column 21,
Line 59, replace "370" with -- 570 --;

Column 23,
Line 17, replace "400" with -- 40 --;

UNITED STATES PATENT AND TRADEMARK OFFICE
CERTIFICATE OF CORRECTION

PATENT NO.    : 6,017,692
DATED         : January 25, 2000
INVENTOR(S)   : Roger Brent et al.

It is certified that error appears in the above-identified patent and that said Letters Patent is hereby corrected as shown below:

<u>Column 48,</u>
Line 50, replace "29" with -- 6 -- and "37" with -- 7 --.

Signed and Sealed this

Fourteenth Day of May, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES:   32

(2) INFORMATION FOR SEQ ID NO:   1:

(i) SEQUENCE CHARACTERISTICS:
      (A) LENGTH: 220
      (B) TYPE:   amino acid
      (C) STRANDEDNESS: Not Relevant
      (D) TOPOLOGY:    linear (xi) SEQUENCE DESCRIPTION: SEQ ID NO: 1:

```
Met Pro Ser Pro Arg Leu Gln His Ser Lys Pro Pro Arg Arg Leu Ser
 1               5                  10                  15

Arg Ala Gln Lys His Ser Ser Gly Thr Ser Asn Thr Ser Thr Ala Asn
                20                  25                  30

Arg Ser Thr His Asn Glu Leu Glu Lys Asn Arg Arg Ala His Leu Arg
            35                  40                  45

Leu Cys Leu Glu Arg Leu Lys Val Leu Ile Pro Leu Gly Pro Asp Cys
        50                  55                  60

Thr Arg His Thr Thr Leu Gly Leu Leu Asn Lys Ala Lys Ala His Ile
65                  70                  75                  80
```

```
Lys Lys Leu Glu Glu Ala Glu Arg Lys Ser Gln His Gln Leu Glu Asn
             85                  90                  95

Leu Glu Arg Glu Gln Arg Phe Leu Lys Trp Arg Leu Glu Gln Leu Gln
            100                 105                 110

Gly Pro Gln Glu Met Glu Arg Ile Arg Met Asp Ser Ile Gly Ser Thr
        115                 120                 125

Ile Ser Ser Asp Arg Ser Asp Ser Glu Arg Glu Ile Glu Val Asp
130                 135                 140

Val Glu Ser Thr Glu Phe Ser His Gly Glu Val Asp Asn Ile Ser Thr
145                 150                 155                 160

Thr Ser Ile Ser Asp Ile Asp Asp His Ser Ser Leu Pro Ser Ile Gly
                165                 170                 175

Ser Asp Glu Gly Tyr Ser Ser Ala Ser Val Lys Leu Ser Phe Thr Ser
            180                 185                 190

Tyr Arg Thr Gln His Asp Ile Thr Val Gln Gly Lys Ile Phe Thr Gly
        195                 200                 205

Pro Ile Gln Tyr Lys Gln Ser Leu Lys Leu Gly Ser
210                 215                 220
```

(2) INFORMATION FOR SEQ ID NO: 2:

(i) SEQUENCE CHARACTERISTICS:
        (A) LENGTH: 2417
        (B) TYPE:   nucleic acid
        (C) STRANDEDNESS: single
        (D) TOPOLOGY:     linear (xi) SEQUENCE DESCRIPTION: SEQ ID NO: 2:

```
AGATTATGAT CGCCTGAGGC CCCTCTCCTA CCCAGATACC GATGTTATAC TGATGTGTTT      60

TTCCTTTTTT TTTTTTTTTT TTTAAGTAAT TAAGGGTAGT TAAATTATTT AAAGTATACA     120

AAGTCCAAAC AGCCAGGGGT AAGGTCTCCA AGAGGCCTTC CCAGGGTAAG GGAGTGCGGA     180

GAGGCCCCGG TCGCCACCCG CGGTGCCCAT GGAGCGGGTG AAGATGATCA ACGTGCAGCG     240

TCTGCTGGAG GCTGCCGAGT TTTTGGAGCG CCGGGAGCGA GAGTGTGAAC ATCGTACGCC     300

TCTTCATTCC CGTCCATGCC GAGCCCCCGA CTGCAGCATT CAAAGCCCCC ACGGAGGTTG     360

AGCCGGGCAC AGAAACACAG CAGCGGGACG AGCAACACCA GCACTGCCAA CAGATCTACA     420

CACAATGAGC TGGAAAAGAA TCGACGAGCT CATCTGCGCC TTTGTTTAGA ACGCTTAAAA     480

GTTCTGATTC CACTAGGACC AGACTGCACC CGGCACACAA CACTTGGTTT GCTCAACAAA     540

GCCAAAGCAC ACATCAAGAA ACTTGAAGAA GCTGAAAGAA AAAGCCAGCA CCAGCTCGAG     600

AATTTGGAAC GAGAACAGAG ATTTTTAAAG TGGCGACTGG AACAGCTGCA GGGTCCTCAG     660

GAGATGGAAC GAATACGAAT GGACAGCATT GGATCAACTA TTTCTTCAGA TCGTTCTGAT     720

TCAGAGCGAG AGGAGATTGA AGTGGATGTT GAAAGCACAG AGTTCTCCCA TGGAGAAGTG     780

GACAATATAA GTACCACCAG CATCAGTGAC ATTGATGACC ACAGCAGCCT GCCGAGTATT     840

GGGAGTGACG AGGGTTACTC CAGTGCCAGT GTCAAACTTT CATTCACTTC ATATAGAACC     900

CAGCATGACA TAACAGTGCA GGGCAAAATA TTCACTGGGC CAATTCAATA CAAACAATCT     960

CTTAAATTGG GTTCATGATG CAGTCTCCTC TTTAAAACAA AACAAACAA AACAAAACTA    1020

TACTTGAACA AAAGGGTCAG AGGACCTGTA TTTAAGCAAA TACTTAGCAA AAAGTGGGGC    1080

AGAGCTCCCA AGGAGAACAA ATATTCAGAA TATTCATATT GGAAAAATCA CAATTTTTAA    1140

TGGCAGCAGA AAACTTGTGT GAAATTTTCT TGATTTGAGT TGATTGAGAA GAGGACATTG    1200

GAGATGCCAT CCTCTTTCTC TTTTCTCGTT TGCTCATACT ACATTGAGTA GACACATTTA    1260
```

-continued

```
AGGATGGGGT TATGAACCCT TCCTGAGCTT TATGGTCCTA AAAGCAAAAT AAAAACTATT    1320

CGAATGAAAA GACAAGAAAA TCAGGTATTA ATCTTGGATA GCTAATAATG AGCTATTAAA    1380

ACTCAGCCTG GGACAGTTTA TCATGAAGCC TGTGGATGAT CAATCCTTTA TTATTATTTT    1440

TTTTTTTTGA AAAAAGCTCA TTTCATGCTC TGCAAAAGGA GAGACTCCCA TGAAGCCTTT    1500

TGAAAGGGAT CATCATGCAG CTCAACTTTC TGTTGGATTC CATGCTAAGC AAGCTAACCT    1560

TATCCTGCAT TGTTAGCACT AGGCACCCAG CTGCCACCTC TCCATCCTGC TGCCCTTAGG    1620

CCACATGGGA GCAGTCCATG CATGACAGCC TCTATCCTAC AAGGCCTATG AGTATGGATT    1680

GGGGGGGCCA AAAGGAAAAA GCTCCATGTG CCTCTTTGTC TGCGTGGGTC AGAAGAGTTG    1740

TGCACGCAGA TTAGCAGGCC AAGGTCTGAG CCACAGCAGC ATTTTTATTT CAGATTTTGA    1800

TAACTGTTTA TATGTGTTGA AAACCAAAAT GACATCTTTT TAAAGCTTAT CCATAAAAAA    1860

AAATAGATGT CTTTTATAGT GGAAAAACAC ATGGGGAAAA AAATCATCTA TTTTGATGCA    1920

GCATTTGATA ATGATAAAAC ACCTCACACC TCACTCTTTA TAGTGCACAA AATGAATGAG    1980

GTCTGGGCTA GGTAGAAAAA GGGTCAATGC TATTTTTGTT TTTAGAATCA TTACCTTTTA    2040

CCAGCTTTTA ACCATCTGAT ATCTATAGTA GACACACTAT CATAGTTAAC ATAGTTAAGT    2100

TCAGCACTTG TCTCATTTTA ATGTAAAGAT TTGCTTCCAT TTTCCTACAG GCAGTCTCTC    2160

TCTTCCTCAC AGTCCCACTG TGCAGGTGCT ATTGTTACTC TTACGAATAT TTTCAGTAAT    2220

GTTATTTTCT TCTAAGTGAA ATTTCTAGCC TGCACTTTGA TGTCATGTGT TCCCTTTGTC    2280

TTTCAAACTC CAAGGTTCCC CTGTGGCCCT CTCCCTTACC CTGGGAAGGC CTCTTGGAGA    2340

CCTTACCCCT GGCTGTTTGG ACTTTGTATA CTTTAAATAA TTTAACTACC CTTAATTACT    2400

TAAAAAAAAA AAAAAA                                                    2417
```

(2) INFORMATION FOR SEQ ID NO:3:

(i) SEQUENCE CHARACTERISTICS:
        (A) LENGTH: 297 amino acids
        (B) TYPE: amino acid
        (D) TOPOLOGY: linear (ii) MOLECULE TYPE: protein (xi) SEQUENCE DESCRIPTION: SEQ ID NO:3:

```
Met Ser Gln Glu Arg Pro Thr Phe Tyr Arg Gln Glu Leu Asn Lys Thr
 1               5                  10                  15

Ile Trp Glu Val Pro Glu Arg Tyr Gln Asn Leu Ser Pro Val Gly Ser
                20                  25                  30

Gly Ala Tyr Gly Ser Val Cys Ala Ala Phe Asp Thr Lys Thr Gly Leu
            35                  40                  45

Arg Val Ala Val Lys Lys Leu Ser Arg Pro Phe Gln Ser Ile Ile His
        50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
```

```
145                 150                 155                 160
Asp Cys Glu Leu Lys Ile Leu Asp Phe Gly Leu Ala Arg His Thr Asp
                165                 170                 175
Asp Glu Met Thr Gly Tyr Val Ala Thr Arg Trp Tyr Arg Ala Pro Glu
            180                 185                 190
Ile Met Leu Asn Trp Met His Tyr Asn Gln Thr Val Asp Ile Trp Ser
        195                 200                 205
Val Gly Cys Ile Met Ala Glu Leu Leu Thr Gly Arg Thr Leu Phe Pro
    210                 215                 220
Gly Thr Asp His Ile Asp Gln Leu Lys Leu Ile Leu Arg Leu Val Gly
225                 230                 235                 240
Thr Pro Gly Ala Glu Leu Leu Lys Lys Ile Ser Ser Glu Ser Ala Arg
                245                 250                 255
Asn Tyr Ile Gln Ser Leu Thr Gln Met Pro Lys Met Asn Phe Ala Asn
            260                 265                 270
Val Phe Ile Gly Ala Asn Pro Leu Gly Lys Leu Thr Ile Tyr Pro His
        275                 280                 285
Leu Met Asp Ile Glu Leu Val Met Ile
    290                 295

(2) INFORMATION FOR SEQ ID NO:4:

(i) SEQUENCE CHARACTERISTICS:
        (A) LENGTH: 1023 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GAATTCCGCA CGAGGCGCCT TCTTGCCCGG CGGCTGCTGG AAAATGTCTC AGGAGAGGCC      60

CACGTTCTAC CGGCAGGAGC TGAACAAGAC AATCTGGGAG GTGCCCGAGC GTTACCAGAA     120

CCTGTCTCCA GTGGGCTCTG GCGCCTATGG CTCTGTGTGT GCTGCTTTTG ACACAAAAAC     180

GGGGTTACGT GTGGCAGTGA AGAAGCTCTC CAGACCATTT CAGTCCATCA TTCATGCGAA     240

AAGAACCTAC AGAGAACTGC GGTTACTTAA ACATATGAAA CATGAAAATG TGATTGGTCT     300

GTTGGACGTT TTTACACCTG CAAGGTCTCT GGAGGAATTC AATGATGTGT ATCTGGTGAC     360

CCATCTCATG GGGGCAGATC TGAACAACAT TGTGAAATGT CAGAAGCTTA CAGATGACCA     420

TGTTCAGTTC CTTATCTACC AAATTCTCCG AGGTCTAAAG TATATACATT CAGCTGACAT     480

AATTCACAGG GACCTAAAAC CTAGTAATCT AGCTGTGAAT GAAGACTGTG AGCTGAAGAT     540

TCTGGATTTT GGACTGGCTC GGCACACAGA TGATGAAATG ACAGGCTACG TGGCCACTAG     600

GTGGTACAGG GCTCCTGAGA TCATGCTGAA CTGGATGCAT ACAACCAGA CAGTTGATAT      660

TTGGTCAGTG GGATGCATAA TGGCCGAGCT GTTGACTGGA AGAACATTGT TCCTGGTAC      720

AGACCATATT GATCAGTTGA AGCTCATTTT AAGACTCGTT GGAACCCCAG GGCTGAGCT      780

TTTGAAGAAA ATCTCCTCAG AGTCTGCAAG AAACTATATT CAGTCTTTGA CTCAGATGCC     840

GAAGATGAAC TTTGCGAATG TATTTATTGG TGCCAATCCC CTGGGTAAGT TGACCATATA     900

TCCTCACCTC ATGGATATTG AATTGGTTAT GATATAAATT GGGGATTTGA AGAAGAGTTT     960

CTCCTTTTGA CCAAATAAAG TACCATTAGT TGAAAAAAAA AAAAAAAAAA AAAAAAAAA     1020

AAA                                                                  1023

(2) INFORMATION FOR SEQ ID NO:     5:
```

```
    (i) SEQUENCE CHARACTERISTICS:
        (A) LENGTH: 9
        (B) TYPE:   amino acid
        (C) STRANDEDNESS: Not Relevant
        (D) TOPOLOGY:    linear (xi) SEQUENCE DESCRIPTION: SEQ ID NO: 5:

Pro Pro Lys Lys Lys Arg Lys Val Ala
1               5

(2) INFORMATION FOR SEQ ID NO:   6:

(i) SEQUENCE CHARACTERISTICS:
        (A) LENGTH: 9
        (B) TYPE:   amino acid
        (C) STRANDEDNESS: Not Relevant
        (D) TOPOLOGY:    linear (xi) SEQUENCE DESCRIPTION: SEQ ID NO: 6:

Tyr Pro Tyr Asp Val Pro Asp Tyr Ala
1               5

(2) INFORMATION FOR SEQ ID NO:   7:

(i) SEQUENCE CHARACTERISTICS:
        (A) LENGTH: 16
        (B) TYPE:   nucleic acid
        (C) STRANDEDNESS: single
        (D) TOPOLOGY:    linear (xi) SEQUENCE DESCRIPTION: SEQ ID NO: 7:

AATTCGGCAC GAGGCG                                                  16

(2) INFORMATION FOR SEQ ID NO:   8:

(i) SEQUENCE CHARACTERISTICS:
        (A) LENGTH: 12
        (B) TYPE:   nucleic acid
        (C) STRANDEDNESS: single
        (D) TOPOLOGY:    linear (xi) SEQUENCE DESCRIPTION: SEQ ID NO: 8:

GCCGTGCTCC GC                                                      12

(2) INFORMATION FOR SEQ ID NO:   9:

(i) SEQUENCE CHARACTERISTICS:
        (A) LENGTH: 26
        (B) TYPE:   nucleic acid
        (C) STRANDEDNESS: single
        (D) TOPOLOGY:    linear (xi) SEQUENCE DESCRIPTION: SEQ ID NO: 9:

GGAAGCAGAC CACGTGGTCT GCTTCC                                       26

(2) INFORMATION FOR SEQ ID NO:   10:

(i) SEQUENCE CHARACTERISTICS:
        (A) LENGTH: 6
        (B) TYPE:   nucleic acid
        (C) STRANDEDNESS: single
        (D) TOPOLOGY:    linear (xi) SEQUENCE DESCRIPTION: SEQ ID NO: 10:

CACGTG                                                              6

(2) INFORMATION FOR SEQ ID NO:   11:
```

(i) SEQUENCE CHARACTERISTICS:
    (A) LENGTH: 16
    (B) TYPE:   nucleic acid
    (C) STRANDEDNESS: single
    (D) TOPOLOGY:     linear (xi) SEQUENCE DESCRIPTION: SEQ ID NO: 11:

GTAATGCATC CAGTTC                                                16

(2) INFORMATION FOR SEQ ID NO:12:

(i) SEQUENCE CHARACTERISTICS:
        (A) LENGTH: 80 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:12:

Asn Arg Ser Thr His Asn Glu Leu Glu Lys Asn Arg Arg Ala His Leu
1               5                   10                  15

Arg Leu Cys Leu Glu Arg Leu Lys Val Leu Ile Arg Leu Gly Pro Asp
            20                  25                  30

Cys Thr Arg His Thr Thr Leu Gly Leu Leu Asn Lys Ala Lys Ala His
        35                  40                  45

Ile Lys Lys Leu Glu Glu Ala Glu Arg Lys Ser Gln His Gln Leu Glu
50                  55                  60

Asn Leu Glu Arg Glu Gln Arg Phe Leu Lys Trp Arg Leu Glu Gln Leu
65                  70                  75                  80

(2) INFORMATION FOR SEQ ID NO:13:

(i) SEQUENCE CHARACTERISTICS:
        (A) LENGTH: 80 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:13:

Lys Arg Arg Thr His Asn Val Leu Glu Arg Gln Arg Arg Asn Glu Leu
1               5                   10                  15

Lys Leu Ser Phe Phe Ala Leu Arg Asp Gln Ile Pro Glu Val Ala Asn
            20                  25                  30

Asn Glu Lys Ala Pro Lys Val Val Ile Leu Lys Lys Ala Thr Glu Tyr
        35                  40                  45

Val Lys Ser Ile Gln Ser Asp Glu His Arg Leu Ile Ala Glu Lys Glu
50                  55                  60

Gln Leu Arg Arg Arg Arg Glu Gln Leu Lys His Lys Leu Glu Gln Leu
65                  70                  75                  80

(2) INFORMATION FOR SEQ ID NO:14:

(i) SEQUENCE CHARACTERISTICS:
        (A) LENGTH: 80 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:14:

```
Lys Arg Arg Thr His Asn Val Leu Glu Arg Gln Arg Asn Glu Leu
1               5                   10                  15

Lys Arg Ser Phe Phe Ala Leu Arg Asp Gln Ile Pro Glu Leu Glu Asn
            20                  25                  30

Asn Glu Lys Ala Pro Lys Val Val Ile Leu Lys Lys Ala Thr Ala Tyr
        35                  40                  45

Tyr Leu Ser Val Gln Ala Glu Glu Gln Lys Leu Ile Ser Glu Glu Asp
    50                  55                  60

Leu Leu Arg Lys Arg Arg Glu Gln Leu Lys His Lys Leu Glu Gln Leu
65              70                  75                  80
```

(2) INFORMATION FOR SEQ ID NO:15:

(i) SEQUENCE CHARACTERISTICS:
        (A) LENGTH: 80 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:15:

```
Arg Arg Arg Asn His Asn Glu Leu Glu Arg Gln Arg Asn Asp Leu
1               5                   10                  15

Arg Ser Ser Phe Leu Thr Leu Arg Asp His Val Pro Glu Leu Val Lys
            20                  25                  30

Asn Glu Lys Ala Ala Lys Val Val Ile Leu Lys Lys Ala Thr Glu Tyr
        35                  40                  45

Val His Ser Leu Gln Ala Glu Glu His Gln Leu Leu Leu Glu Lys Glu
    50                  55                  60

Lys Leu Gln Ala Arg Gln Gln Gln Leu Leu Lys Lys Ile Glu His Ala
65              70                  75                  80
```

(2) INFORMATION FOR SEQ ID NO:16:

(i) SEQUENCE CHARACTERISTICS:
        (A) LENGTH: 80 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:16:

```
Lys Arg Lys Asn His Asn Phe Leu Glu Arg Lys Arg Arg Asn Asp Leu
1               5                   10                  15

Arg Ser Arg Phe Leu Ala Leu Arg Asp Gln Val Pro Thr Leu Ala Ser
            20                  25                  30

Cys Ser Lys Ala Pro Lys Val Val Ile Leu Ser Lys Ala Leu Glu Tyr
        35                  40                  45

Leu Gln Ala Leu Val Gly Ala Glu Lys Arg Met Ala Thr Glu Lys Arg
    50                  55                  60

Gln Leu Arg Cys Arg Gln Gln Gln Leu Gln Lys Arg Ile Ala Tyr Leu
65              70                  75                  80
```

(2) INFORMATION FOR SEQ ID NO:17:

(i) SEQUENCE CHARACTERISTICS:
        (A) LENGTH: 79 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:17:

```
Lys Arg Ala His His Asn Ala Leu Glu Arg Lys Arg Asp His Ile
1               5                   10                  15

Lys Asp Ser Phe His Ser Leu Arg Asp Ser Val Pro Ser Leu Gln Gly
            20                  25                  30

Gln Lys Ala Ser Lys Ala Gln Ile Leu Asp Lys Ala Thr Glu Tyr Ile
            35                  40                  45

Gln Tyr Met Arg Arg Lys Asn His Arg His Gln Gln Asp Ile Asp Asp
50                      55                  60

Leu Lys Arg Gln Asn Ala Leu Leu Glu Gln Gln Val Arg Ala Leu
65                  70                  75
```

(2) INFORMATION FOR SEQ ID NO:18:

(i) SEQUENCE CHARACTERISTICS:
        (A) LENGTH: 79 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:18:

```
Arg Arg Glu Ala Ile Asn Ser Asn Glu Arg Arg Met Gln Ser Ile
1               5                   10                  15

Asn Ala Gly Phe Gln Ser Leu Lys Thr Leu Lys Pro His Thr Asp Gly
            20                  25                  30

Glu Lys Leu Ser Lys Ala Ala Ile Leu Gln Gln Thr Ala Glu Tyr Ile
            35                  40                  45

Phe Ser Leu Glu Gln Glu Lys Thr Arg Leu Leu Gln Gln Asn Thr Gln
50                      55                  60

Leu Lys Arg Phe Ile Gln Glu Leu Ser Gly Ser Ser Pro Lys Arg
65                  70                  75
```

(2) INFORMATION FOR SEQ ID NO:19:

(i) SEQUENCE CHARACTERISTICS:
        (A) LENGTH: 83 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:19:

```
Lys Lys Asp Asn His Asn Leu Ile Glu Arg Arg Arg Phe Asn Ile
1               5                   10                  15

Asn Asp Arg Ile Lys Glu Leu Gly Thr Leu Ile Pro Lys Ser Ser Asp
            20                  25                  30

Pro Gln Met Arg Trp Asn Gly Thr Ile Leu Lys Ala Ser Val Asp Tyr
            35                  40                  45

Ile Arg Lys Leu Gln Lys Glu Gln Gln Ser Lys Asp Arg Leu Glu Ser
50                      55                  60

Arg Gln Arg Ser Leu Glu Gln Ala Asn Arg Ser Leu Gln Leu Arg Ile
65                  70                  75                  80

Gln Glu Leu
```

(2) INFORMATION FOR SEQ ID NO:20:

(i) SEQUENCE CHARACTERISTICS:
    (A) LENGTH: 360 amino acids
    (B) TYPE: amino acid
    (C) STRANDEDNESS: Not Relevant
    (D) TOPOLOGY: linear (ii) MOLECULE TYPE: protein (xi) SEQUENCE DESCRIPTION: SEQ ID NO:20:

```
Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
            35                  40                  45

Arg Val Ala Val Lys Lys Leu Ser Arg Pro Phe Gln Ser Ile Ile His
        50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
                100                 105                 110

Leu Asn Asn Ile Val Lys Cys Gln Lys Leu Thr Asp Asp His Val Gln
            115                 120                 125

Phe Leu Ile Tyr Gln Ile Leu Arg Gly Leu Lys Tyr Ile His Ser Ala
130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
                180                 185                 190

Ile Met Leu Asn Trp Met His Tyr Asn Gln Thr Val Asp Ile Trp Ser
            195                 200                 205

Val Gly Cys Ile Met Ala Glu Leu Leu Thr Gly Arg Thr Leu Phe Pro
210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Ser
                245                 250                 255

Phe Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
290                 295                 300

His Ala Tyr Phe Ala Gln Tyr His Asp Pro Asp Asp Glu Pro Val Ala
305                 310                 315                 320

Asp Asp Tyr Asp Gln Ser Phe Glu Ser Arg Asp Leu Leu Tyr Asp Glu
                325                 330                 335

Trp Lys Ser Leu Thr Tyr Asp Glu Val Ile Ser Phe Val Pro Pro Pro
                340                 345                 350

Leu Asp Gln Glu Glu Met Glu Ser
                355                 360
```

(2) INFORMATION FOR SEQ ID NO:21:

(i) SEQUENCE CHARACTERISTICS:
        (A) LENGTH: 416 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:21:

```
Met Met Thr Thr Asn Glu Glu Phe Ile Arg Thr Gln Ile Phe Gly Thr
1               5                   10                  15

Val Phe Glu Ile Thr Asn Arg Tyr Asn Asp Leu Asn Pro Val Gly Met
            20                  25                  30

Gly Ala Phe Gly Leu Val Cys Ser Ala Thr Asp Thr Leu Thr Ser Gln
        35                  40                  45

Pro Val Ala Val Lys Lys Ile His Lys Pro Phe Ser Thr Ala Val Leu
    50                  55                  60

Ala Lys Arg Thr Tyr Arg Glu Leu Lys Leu Leu Lys His Leu Arg His
65                  70                  75                  80

Glu Asn Leu Ile Cys Leu Gln Asp Ile Phe Ser Pro Leu Glu Asn Asp
                85                  90                  95

Ile Tyr Phe Val Thr Glu Leu Gln Gly Thr Asp Leu His Arg Leu Leu
            100                 105                 110

Gln Thr Arg Pro Leu Glu Lys Gln Phe Val Gln Tyr Phe Leu Tyr Gln
        115                 120                 125

Ile Leu Arg Gly Leu Lys Tyr Val His Ser Ala Gly Val Ile His Arg
    130                 135                 140

Asp Leu Lys Pro Ser Asn Ile Leu Ile Asn Glu Asn Cys Asp Leu Lys
145                 150                 155                 160

Ile Cys Asp Phe Gly Leu Ala Arg Ile Gln Asp Pro Gln Met Thr Gly
                165                 170                 175

Tyr Val Ser Thr Arg Tyr Tyr Arg Ala Pro Glu Ile Met Leu Thr Trp
            180                 185                 190

Gln Lys Tyr Asp Val Glu Val Asp Ile Trp Ser Ala Gly Cys Ile Phe
        195                 200                 205

Ala Glu Met Ile Glu Gly Lys Phe Leu Phe Pro Gly Lys Asp His Val
    210                 215                 220

His Gln Phe Ser Ile Ile Thr Asp Leu Leu Gly Ser Pro Pro Lys Asp
225                 230                 235                 240

Val Ile Asn Thr Ile Cys Ser Glu Asn Thr Leu Lys Phe Val Thr Ser
                245                 250                 255

Leu Pro His Arg Asp Pro Ile Pro Phe Ser Glu Arg Phe Lys Thr Val
            260                 265                 270

Glu Pro Asp Ala Val Asp Leu Leu Glu Lys Met Leu Val Phe Asp Pro
        275                 280                 285

Lys Lys Arg Ile Thr Ala Ala Asp Ala Leu Ala His Pro Tyr Ser Ala
    290                 295                 300

Pro Tyr His Asp Pro Thr Asp Glu Pro Val Ala Asp Ala Lys Phe Asp
305                 310                 315                 320

Trp His Phe Asn Asp Ala Asp Leu Pro Val Asp Thr Trp Arg Val Met
                325                 330                 335

Tyr Ser Glu Ile Leu Asp Phe Met Lys Ile Cys Cys Glu Asp Cys Gln
            340                 345                 350

Ile Asp Ile Ser Ala Thr Phe Asp Asp Gln Val Ala Ala Ala Thr Ala
    355                 360                 365
```

Ala Ala Ala Gln Ala Gln Ala Gln Ala Gln Val Gln Leu Asn
        370             375             380

Met Ala Ala His Ser His Asn Gly Ala Gly Thr Thr Gly Asn Asp His
385             390             395             400

Ser Asp Ile Ala Gly Gly Asn Lys Gly Gln Arg Ser Cys Ser Cys Lys
                405             410             415

(2) INFORMATION FOR SEQ ID NO:22:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:22:

Asn Glu Leu Lys Arg Ser Phe Phe Ala Leu Arg Asp Gln Ile Pro Glu
1               5                   10                  15

Leu Glu Asn Asn Glu Lys Ala Pro Lys Val Val Ile Leu Lys Lys Ala
                20                  25                  30

Thr Ala Tyr Ile Leu Ser Val
            35

(2) INFORMATION FOR SEQ ID NO:23:

(i) SEQUENCE CHARACTERISTICS:
        (A) LENGTH: 36 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:23:

Asp His Ile Asp Gln Leu Lys Leu Ile Leu Arg Leu Val Gly Thr Pro
1               5                   10                  15

Gly Ala Glu Leu Leu Lys Lys Ile Ser Ser Glu Ser Ala Arg Asn Tyr
                20                  25                  30

Ile Gln Ser Leu
            35

(2) INFORMATION FOR SEQ ID NO:24:

(i) SEQUENCE CHARACTERISTICS:
        (A) LENGTH: 45 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:24:

Asp His Ile Lys Asp Ser Phe His Ser Leu Arg Asp Ser Val Pro Ser
1               5                   10                  15

Leu Arg Asp Ser Val Pro Ser Leu Gln Gly Gln Lys Ala Ser Lys Ala
                20                  25                  30

Gln Ile Leu Asp Lys Ala Thr Glu Tyr Ile Gln Tyr Met
            35                  40                  45

(2) INFORMATION FOR SEQ ID NO:25:

(i) SEQUENCE CHARACTERISTICS:

(A) LENGTH: 15 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:25:

Leu Thr Ile Thr Pro His Leu Met Asp Ile Glu Leu Val Met Ile
1               5                   10                  15

(2) INFORMATION FOR SEQ ID NO:26:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:26:

Leu Thr Phe Asn Pro His Lys Arg Ile Glu Val Glu Gln
1               5                   10

(2) INFORMATION FOR SEQ ID NO:27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

AGCTACTCTA GAGATGTCTC AGGAGAGGCC CAC                              33

(2) INFORMATION FOR SEQ ID NO:28:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

AAGGAAAAAA GCGGCCGCAA TTTATATCAT AACCAATTC                        39

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

TGGGTAAGTT GACCATATAT C                                           21

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single -continued (D) TOPOLOGY: linear (ii) MOLECULE TYPE: DNA (genomic)

(xi) SEQUENCE DESCRIPTION: SEQ ID NO:30:

CAACTAATGG TACTTTATTT                                           20

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

TGGCTGTCGA CTTGCTGGAG AAGAT                                     25

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

GGCACTTGAA TAATATTTGG AGAGT                                     25